United States Patent [19]

Shiokawa et al.

[11] Patent Number: 4,988,723

[45] Date of Patent: Jan. 29, 1991

[54] BENZOPYRAN DERIVATIVES AND THEIR USE AS ANTI-HYPERTENSIVES

[75] Inventors: Youichi Shiokawa, Ibaraki; Koichi Takimoto, Takarazuka; Kohei Takenaka, Sakai; Takeshi Kato, Ikeda, all of Japan

[73] Assignee: Fujisawa Pharmaceutical Co., Ltd., Osaka, Japan

[21] Appl. No.: 352,990

[22] Filed: May 17, 1989

[30] Foreign Application Priority Data

Jun. 2, 1988 [GB] United Kingdom ............... 8813044
Aug. 16, 1988 [GB] United Kingdom ............... 8819449
Jan. 4, 1989 [GB] United Kingdom ............... 8900089

[51] Int. Cl.$^5$ .................. A61K 31/425; A61K 31/35; C07D 413/04; C07D 417/04
[52] U.S. Cl. .................................... 514/392; 514/183; 514/210; 514/218; 514/227.2; 514/228.8; 514/370; 514/377; 514/456; 540/202; 540/467; 540/470; 540/544; 540/553; 544/55; 544/96; 544/332; 548/193; 548/233; 548/234; 548/316; 549/399; 549/404; 549/419
[58] Field of Search ............... 548/193, 194, 233, 316, 548/234, 951; 514/370, 377, 392, 456, 183, 210, 218, 227.2, 228.8; 549/399, 404, 419; 540/202, 467, 470, 544, 553; 544/55, 96, 332

[56] References Cited

U.S. PATENT DOCUMENTS

| | | | |
|---|---|---|---|
| 4,481,213 | 11/1984 | Evans | 549/399 |
| 4,496,565 | 1/1985 | Evans et al. | 514/222 |
| 4,571,406 | 2/1986 | Evans | 514/456 |
| 4,575,511 | 3/1986 | Evans | 514/456 |
| 4,610,992 | 9/1986 | Evans | 514/320 |
| 4,629,734 | 12/1986 | Ashwood | 514/456 |
| 4,631,282 | 12/1986 | Cassidy | 514/254 |
| 4,677,116 | 6/1987 | Evans | 514/456 |
| 4,687,779 | 8/1987 | Evans | 514/456 |

FOREIGN PATENT DOCUMENTS

| | | |
|---|---|---|
| 0076075 | 4/1983 | European Pat. Off. |
| 0093534 | 11/1983 | European Pat. Off. |
| 0095316 | 11/1983 | European Pat. Off. |
| 0120428 | 10/1984 | European Pat. Off. |
| 0173848 | 3/1986 | European Pat. Off. |
| 972003 | 10/1964 | United Kingdom ............... 548/316 |

Primary Examiner—Mary C. Lee
Assistant Examiner—Jacqueline Haley
Attorney, Agent, or Firm—Oblon, Spivak, McClelland, Maier & Neustadt

[57] ABSTRACT

Benzopyran derivatives of formula (I) wherein the substituents are as defined herein are provided. The compounds possess vasodilating activity and are useful in the treatment of hypertension. Pharmaceutical compositions and methods of treating hypertension are also provided.

15 Claims, No Drawings

BENZOPYRAN DERIVATIVES AND THEIR USE AS ANTI-HYPERTENSIVES

The present invention relates to novel benzopyran derivatives. More particularly, it relates to novel benzopyran derivatives which have vasodilating activity, to processes for preparation thereof, to a pharmaceutical composition comprising the same and to a use of the same as a medicament in the treatment of diseases such as hypertension in human being or animals.

Accordingly, one object of the present invention is to provide novel benzopyran derivatives, which are useful as a vasodilating agent.

Another object of the present invention is to provide processes for preparation of said benzopyran derivatives.

A further object of the present invention is to provide a pharmaceutical composition comprising, as an active ingredient, said benzopyran derivatives.

Still further object of the present invention is to provide a use of said benzopyran derivatives as a medicament in the treatment of diseases such as hypertension in human being or animals.

The benzopyran derivatives of the present invention are novel and can be represented by the formula (I):

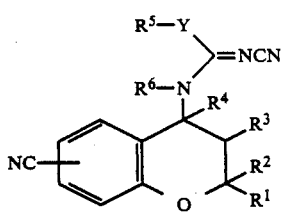
(I)

wherein
$R^1$ and $R^2$ are each lower alkyl,
$R^3$ is hydroxy or acyloxy and $R^4$ is hydrogen or
$R^3$ and $R^4$ are linked together to form a bond, and
(i) Y is —S—, —O— or a group of the formula:

wherein $R^7$ is hydrogen, acyl or lower alkyl which may have suitable substituent(s), and
$R^5$ and $R^6$ are each hydrogen or lower alkyl,
(ii) Y is as defined above, and
$R^5$ and $R^6$ are linked together to form lower alkylene, or
(iii) Y-$R^5$ is a heterocyclic group which may have suitable substituent(s), and
$R^6$ is hydrogen or lower alkyl.

With regard to the compound (I) of the present invention, it is to be noted that there may be one or more stereo-isomeric pairs due to the presence of one or more asymmetric carbon atom(s) or double bond and these isomers or a mixture thereof are included within a scope of the compound (I) of the present invention.

According to the present invention, the object compound (I) can be prepared by the following processes:

Process 1:

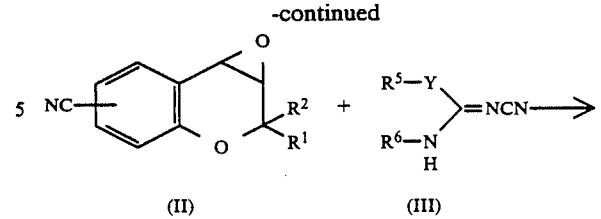

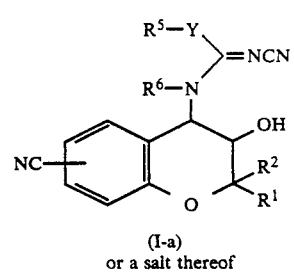

Process 2:

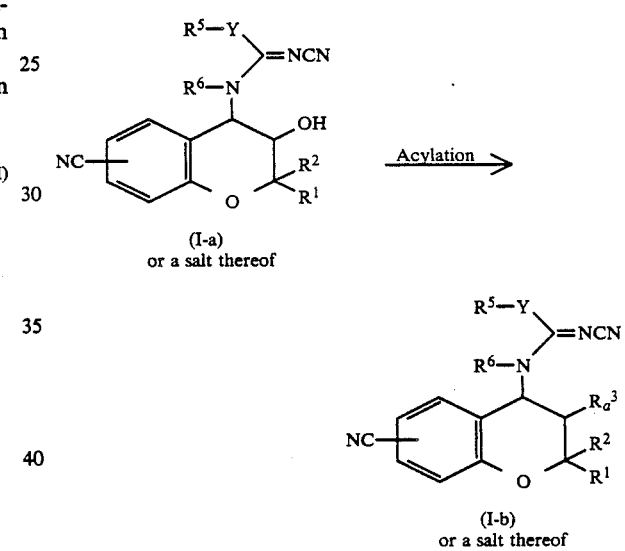

Process 3:

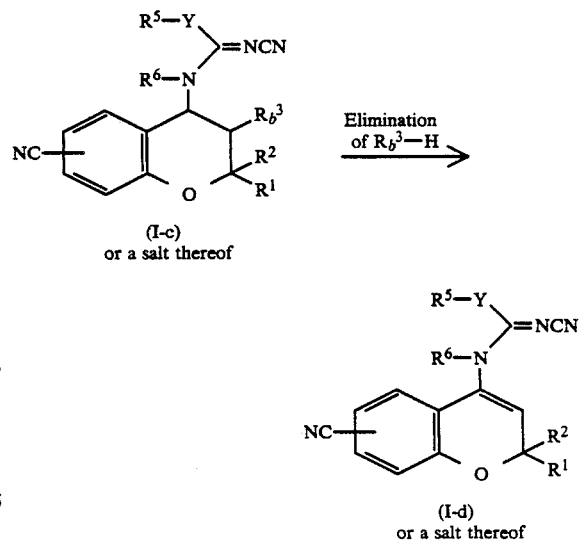

Process 4:

-continued (I-e) or a salt thereof + (IV) $R_a^7-X_a \longrightarrow$ (I-f) or a salt thereof Process 5:

(V) or a salt thereof + (VI) → (I-g) or a salt thereof

Process 6

(I-h) or a salt thereof + (VIII) R⁸—H → or a salt thereof (I-i) or a salt thereof Process 7:

(I-j) or a salt thereof + (VIII) $R_a^6-X_b \longrightarrow$ (I-k) or a salt thereof wherein
$R^1$, $R^2$, $R^3$, $R^5$, $R^6$ and Y are each as defined above,
$R_a^3$ is acyloxy,
$R_b^3$ is hydroxy or acyloxy,
$R_a^5$ and $R_a^6$ are each lower alkyl,
$R_a^7$ is acyl or lower alkyl which may have suitable substituent(s),
$R^8$ is a group of the formula:

$$-N\begin{matrix}R^7\\R^5\end{matrix}$$

wherein
$R^5$ is hydrogen or lower alkyl, and
$R^7$ is as defined above;
1-pyrrolidinyl; morpholino; piperidino; 1-piperadinyl which may have suitable substituent(s); or lower alkoxy,
$X_a$ and $X_b$ are each an acid residue, and
Z is a leaving group.

Suitable salts of the compound (I), (I-a), (I-b), (I-c), (I-d), (I-e), (I-f), (I-g), (I-h), (I-i), (I-j), (I-k), (III), (V) and (VII) are conventional non-toxic, pharmaceutically acceptable salts and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, t-butyl, pentyl, hexyl, or the like.

Suitable "lower alkylene" formed by linkage of $R^5$ and $R^6$ may include methylene, ethylene, propylene, trimethylene, tetramethylene, 1,1-dimethylethylene, pentamethylene, hexamethylene, or the like.

Suitable "a heterocyclic group which may have suitable substituent(s)" may include 5- or 6-membered heteromonocyclic group containing at least one hetero atom such as nitrogen atom, for example, pyrrolidinyl, morpholinyl, piperidyl, piperadinyl, and the like, which may have a substituent such as lower alkyl as exemplified above, and the most preferred example may be 1-pyrrolidinyl, morpholino, piperidino and 4-(lower)alkyl-1-piperadinyl as exemplified below.

Suitable "1-piperadinyl which may have suitable substituent(s)" may include 1-piperadinyl; 4-lower alkyl-1-piperadinyl (e.g. 4-methyl-1-piperadinyl, 4-ethyl-1-piperadinyl, 4-propyl-1-piperadinyl, 4-isopropyl-1-piperadinyl, 4-butyl-1-piperadinyl, etc.), and the like.

Suitable "lower alkoxy" may include methoxy, ethoxy, propoxy, isopropoxy, butoxy, isobutoxy, tert-butoxy, pentyloxy, tert-pentyloxy, hexyloxy, and the like, preferably one having 1 to 4 carbon atom(s).

Suitable "an acid residue" may include halogen [e.g. fluoro, chloro, bromo, iodo], acyloxy [e.g. tosyloxy, mesyloxy, etc.] and the like.

Suitable "acyl" and acyl moiety of "acyloxy" is conventional one used in a pharmaceutical field and may include organic carboxylic acyl and organic sulfonic acyl such as lower alkanoyl (e.g. formyl, acetyl, propionyl, butyryl, valeryl, etc.), arenesulfonyl (e.g. benzenesulfonyl, toluenesulfonyl, etc.), lower alkanesulfonyl (e.g. methanesulfonyl, ethanesulfonyl, etc.), and the like.

Suitable "lower alkyl which may have suitable substituents)" is conventional one used in a pharmaceutical field and may include lower alkyl (e.g. methyl, ethyl, propyl, isopropyl, butyl, t-butyl, pentyl, hexyl, etc.), substituted or unsubstituted ar(lower)alkyl such as mono or di or triphenyl(lower)alkyl which may have suitable substituent(s) (e.g. trityl, benzyl, phenethyl, benzhydryl, p-nitrobenzyl, etc.), and the like.

Suitable "leaving group" may include lower alkylthio (e.g. methylthio, ethylthio, etc.), and the like.

The processes 1 to 7 for preparing the object compound (I) of the present invention are explained in detail in the following.

Process 1:

The object compound (I-a) or a salt thereof can be prepared by reaction the compound (II) with the compound (III) or a salt thereof.

The present reaction is usually carried out in the presence of a base such as alkali lithium (e.g. n-butyl lithium, etc.), alkali metal hydride (e.g. sodium hydride, potassium hydride, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

The object compound (I-a) can be used as a starting compound of the Process 2 mentioned hereinbelow with or without isolation.

Process 2:

The object compound (I-b) or a salt thereof can be prepared by acylating the compound (I-a) or a salt thereof.

The acylating agent used in this reaction is a conventional one which is capable of introducing the acyl group as mentioned above into a hydroxy, and may preferably be lower alkanecarboxylic acid, arenesulfonic acid, lower alkanesulfonic acid, their acid anhydride, their acid halide, their activated ester, their acid amide, and the like.

In case that the acylating agent is used in a free acid form, the reaction is usually carried out in the presence of a conventional condensing agent such as carbodiimide compounds, and the like.

This reaction is preferably carried out in the presence of a base such as those given in the explanation of the Process 1 mentioned above.

This reaction is usually carried out in a solvent such as dimethylformamide, tetrahydrofuran, pyridine or any other solvent which does not adversely affect the reaction.

The reaction temperature is not critical, and the reaction can be carried out under cooling to warming.

Process 3:

The object compound (I-d) or a salt thereof can be prepared by subjecting the compound (I-c) or a salt thereof to elimination reaction of the compound $R_b^3$-H.

The elimination reaction can usually be carried out by an inorganic base such as alkali metal hydride (e.g. sodium hydride, potassium hydride, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.2]octane, 1,5-diazabicyclo[5.4.0]undec-5-ene, 1,8-diazabicyclo[5.4.0]undec-7-ene or the like.

This reaction can be carried out in a conventional solvent which does not adversely affect the reaction such as those given in the explanation of Process 1.

The reaction temperature is not critical and the reaction is usually carried out under cooling, at ambient temperature or under heating.

Process 4:

The object compound (I-f) or a salt thereof can be prepared by reacting the compound (I-e) or a salt thereof with the compound (IV).

This reaction is usually carried out in a solvent such as alcohol [e.g. methanol, ethanol, etc.], N,N-dimethylformamide or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

Process 5:

The object compound (I-g) or a salt thereof can be prepared by reacting the compound (V) or a salt thereof with the compound (VI).

This reaction is usually carried out in a solvent such as alcohol [e.g. methanol, ethanol, etc.], N,N-dimethylformamide, tetrahydrofuran or any other solvent which does not adversely affect the reaction.

The reaction may be carried out in the presence of an inorganic or an organic base such as tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under warming or heating.

Process 6:

The object compound (I-i) or a salt thereof can be prepared by reacting the compound (I-h) or a salt thereof with the compound (VII) or a salt thereof.

The reaction may be carried out in the presence of an inorganic or an organic base such as tri(lower)alkylamine [e.g. trimethylamine, triethylamine, etc.], pyridine or its derivative [e.g. picoline, lutidine, 4-dimethylaminopyridine, etc.], or the like.

This reaction is usually carried out in a solvent such as alcohol [e.g. methanol, ethanol, etc.], dimethyl sulfoxide, N,N-dimethylformamide, tetrahydrofuran or any other solvent which does not adversely affect the reaction.

In case that the compound (VII), or a salt thereof or the base to be used is liquid, it can also be used as a solvent.

The reaction temperature is not critical, and the reaction can be carried out under warming or heating.

Process 7:

The object compound (I-k) or a salt thereof can be prepared by reacting the compound (I-j) or a salt thereof with the compound (VIII).

This reaction can be carried out in substantially the same manner as Process 4, and therefore the reaction mode and reaction conditions [e.g. solvents, bases, reaction temperature, etc.] of this reaction are to be referred to those as explained in Process 4.

Among the starting compounds (II), (III), (IV), (V), (VI), (VII) and (VIII), some of them are new and such compounds can be prepared by the methods of Preparations mentioned below.

The object compound (I) of the present invention can be isolated and purified in a conventional manner, for example, extraction, precipitation, fractional crystallization, recrystallization, chromatography, and the like.

With regard to the compound (I) of the present invention, when $R^3$ is hydroxy or acyloxy and $R^4$ is hydrogen, it is preferred that the hydroxy at the third position of 1-benzopyran nucleus and a group of the formula:

$$\begin{array}{c} R^5-Y \\ \phantom{xx} \diagdown \\ R^6-N \\ \phantom{xx} | \end{array} \!\!\!\!\!\! \Big\rangle\!\!=\!\!NCN$$

at the fourth position of the same are mutually trans, and further it is most preferred they being the (3S,4R)-isomer.

The optical resolution of the isomers of the compound (I) can be carried out by a conventional method such as a resolution by reacting a mixture of isomers with an optically active reagent. Such reagents include optically active acids (e.g., benzyloxycarbonyl-L-phenylalanine, etc.) or acid derivatives such as acid chloride (e.g., l-menthoxyacetyl chloride, etc.) or acid anhydride and the like.

With regard to the starting compound (V) for the compound (I) of the present invention, it may be used after being carried out the optical resolution of the isomers of the compound (V).

With regard to the most preferred (3S,4R)-isomer of the compound (I), it can be prepared from (3S,4S)-isomer of the compound (II) in a manner of Process 1 or (3S,4R)-isomer of the compound (V) in a manner of Process 5, and these stereospecific isomers can be prepared from the compound (IX) by the following steps.

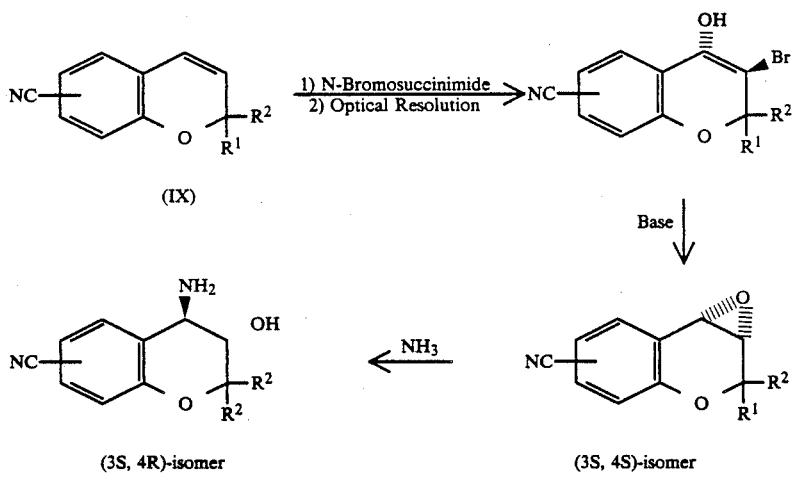

wherein $R^1$ and $R^2$ are each as defined above.

These reactions can be carried out by conventional methods and the optical resolution can preferably carried out using an optically active reagent such as N-protected optically active amino acid (e.g. benzyloxycarbonyl-L-alanine, benzyloxycarbonyl-L-proline, etc.), optically active carboxylic acid (e.g. 2-acetoxypropionic acid, camphoric acid, 2-phenylbutanoic acid, etc.) and the like.

Further, the (3S,4R)-isomer of the compound (V) can also be prepared from a mixture of its (3S,4R) and (3R,4S) isomers by an optical resolution method, for example, as mentioned in Preparation of the present specification.

The object compounds (I) of the present invention are novel and exhibit vasodilating activity and long duration, and are of use for treating diseases such as hypertension.

In order to illustrate the usefulness of the object compound (I), hypotensive activity of representative compounds of the present invention are shown below.

(1) Effect on normotensive rats

Test Compound trans-4-(2-Cyanoimino-3-methylimidazolidin-1-yl)-3,4-dihydro-3-hydroxy-2,2-dimethyl-2H-1-benzopyran-6-carbonitrile Test Method Male Wistar strain rats aged 10–11 weeks, weighing about 250 g were used after going unfed overnight. Under ether anesthesia, polyethylene cannula were inserted in the femoral artery for measuring blood pressure and in the femoral vein for injection of the test compound. About 2 hours after the operation, test compound was given intravenously. Blood pressure was measured at the femoral artery by means of a pressure transducer and recorded as electrically integrated values of mean arterial pressure.

Test Result

Mean ratios of maximum decrease of blood pressure (mmHg) are shown in table.

| Dose (mg/kg) | Effect Max (%) |
|---|---|
| 1.0 | 48.0 |

Effect on spontaneous hypertensive rats

Test Compound (3S,4R)-4-(2-Cyanoiminothiazolidin-3-yl)-3,4-dihydro-3-hydroxy-2,2-dimethyl-2H-1-benzopyran-6-carbonitrile Test Method 14 to 17-week-old male spontaneous hypertensive rats with mean arterial blood pressure of about 150 mmHg, weighing 300–375 g, were used. The animals were cannulated in the left femoral artery and the mean blood pressure and heart rate were measured with a pressure-transducer. The drugs were given orally. The animals were deprived of food for about 18 hours before oral dosing. The test drugs were suspended in 0.5% methylcellulose, and given in oral dose of 0.1 mg/kg and 1.0 mg/kg.

Test Result

Mean ratios and the duration of half (T ½) of maximum decrease of blood pressure (mmHg) are shown in Table.

| Dose (mg/kg) | Effect max (%) | T ½ (minutes) |
|---|---|---|
| 0.1 | 20.7 | 135 |
| 1.0 | 60.0 | 225 |

For therapeutic administration, the object compounds (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general amounts between 1 mg and about 1,000 mg or even more per day may be administered to a patient. An average single dose of about 1 mg, 2 mg, 5 mg, 10 mg, 25 mg, 50 mg, 100 mg, 200 mg of the object compound (I) of the present invention may be used in treating diseases.

The following Preparations and Examples are given for the purpose of illustrating the present invention.

Preparation 1

Dimethyl N-cyanoimidodithiocarbonate (14.62 g) was added in small portion at ambient temperature to a solution of 1,3-diaminopropane (9.64 g) in tetrahydrofuran (80 ml). The reaction mixture was stirred for 3 hours at the same temperature. The forming precipitate was filtered off, washed with tetrahydrofuran to give 2-cyanoiminohexahydropyridimidine (10.28 g).

mp: 176° to 184° C.
IR (Nujol): 3320, 3270, 2160, 1635, 1580 cm$^{-1}$
NMR (DMSO-d$_6$, δ): 1.72 (2H, quintet, J=6 Hz), 3.12 (4H, t, J=6 Hz), 7.29 (2H, br s)
MASS: 124, 68, 56

Preparation 2

The following compound was obtained according to a similar manner to that of Preparation 1.
2-Cyanoimino-1-methylhexahydropyrimidine
mp: 156° to 158° C.
IR (Nujol): 3280, 2175, 2150 cm$^{-1}$
NMR (DMSO-d$_6$, δ): 1.84 (2H, quintet, J=6 Hz), 3.91 (3H, s), 3.10-3.50 (4H, m), 7.26 (1H, br s)
MASS: 138

Preparation 3

A mixture of trans-4-amino-3,4-dihydro-2,2-dimethyl-3-hydroxy-2H-1-benzopyran-6-carbonitrile (193 g) and (−)-di-p-toluoyl-L-tartaric acid monohydrate (358 g) was dissolved in ethanol (600 ml) under reflux. The mixture was cooled to room temperature and stood for 3 days to give a white precipitate. This precipitate was collected by filtration, washed with a small volume of ethanol, and recrystallized twice from ethanol to give (−)-di-p-toluoyl-L-tartaric acid salt of (3S,4R)-4-amino-3,4-dihydro-3-hydroxy-2,2-dimethyl-2H-1-benzopyran-6-carbonitrile (43.1 g).

mp: 175°–176° C.
IR (Nujol): 3510, 3390, 3210, 2720, 2625, 2230, 1710, 1610 cm$^{-1}$
NMR (DMSO-d$_6$, δ): 1.05 (3H, s), 1.37 (3H, s), 2.34 (6H, s), 3.57 (1H, d, J=9 Hz), 4.12 (1H, d, J=9 Hz), 5.66 (2H, s), 6.92 (1H, d, J=9 Hz), 7.27 (4H, d, J=8 Hz), 7.63 (1H, dd, J=9 Hz, 2 Hz), 7.83 (4H, d, J=8 Hz), 7.98 (1H, d, J=2 Hz), 6.7–8.2 (5H, br)
$[\alpha]_D^{24}$: −55.9° (C=1.0, ethanol)

Preparation 4

A solution of (−)-di-p-toluoyl-L-tartaric acid salt of (3S,4R)-4-amino-3,4-dihydro-3-hydroxy-2,2-dimethyl-2H-1-benzopyran-6-carbonitrile (42.0 g) in methanol (500 ml) was passed through a column of an anion exchange resin "IRA-910" (trademark, made by Japan Organo Co., Ltd.), and then eluted with methanol (1.7 l). The eluate was concentrated under reduced pressure to give (3S,4R)-4-amino-3,4-dihydro-3-hydroxy-2,2-dimethyl-2H-1-benzopyran-6-carbonitrile (15.09 g).

IR (CHCl$_3$, δ): 3400, 2220, 1605, 1570 cm$^{-1}$
NMR (DMSO-d$_6$, δ): 1.12 (3H, s), 1.40 (3H, s), 2.02 (2H, br s), 3.21 (1H, d, J=9.4 Hz), 3.55 (1H, d, J=9.4 Hz), 5.58 (1H, s), 6.86 (1H, d, J=8.5 Hz), 7.55 (1H, dd, J=8.5 Hz, 2 Hz), 7.97 (1H, d, J=2 Hz)
$[\alpha]_D^{23}$ = 81.00° (C=1, ethanol)

Preparation 5

A mixture of trans-4-amino-3,4-dihydro-3-hydroxy-2,2-dimethyl-2H-1-benzopyran-6-carbonitrile (32.74 g) and (+)-di-p-toluoyl-D-tartaric acid (57.95 g) was dissolved in ethanol (85 ml) under reflux. The mixture was cooled to room temperature and stood for 4 days to give a white precipitate. This precipitate was collected by filtration, washed with a mixture of ethanol and diisopropyl ether (100 ml, 1:2), and recrystallized from ethanol (80 ml) to give (+)-di-p-toluoyl-D-tartaric acid salt of (3R,4S)-4-amino-3,4-dihydro-3-hydroxy-2,2-dimethyl-2H-1-benzopyran-6-carbonitrile (19.20 g).

mp: 176° to 178.5° C.
IR (Nujol): 3520, 3390, 3210, 2720, 2625, 2230, 1705, 1610 cm$^{-1}$
NMR (DMSO-d$_6$, δ): 1.05 (3H, s), 1.39 (3H, s), 2.37 (6H, s), 3.60 (1H, d, J=9 Hz), 4.14 (1H, d, J=9 Hz), 5.69 (2H, s), 6.95 (1H, d, J=9 Hz), 7.32 (4H, d, J=8 Hz), 7.67 (1H, dd, J=9 Hz), 7.87 (4H, d, J=8 Hz), 8.00 (1H, br s)

Preparation 6

(+)-di-p-Toluoyl-D-tartaric acid salt of (3R,4S)-4-amino-3,4-dihydro-3-hydroxy-2,2-dimethyl-2H-1-benzopyran-6-carbonitrile (6.32 g) was neutralized with a saturated aqueous sodium bicarbonate solution and extracted four times with ethyl acetate. The ethyl acetate extracts were combined, dried over anhydrous magnesium sulfate, and then concentrated in vacuo to give (3R,4S)-4-amino-3,4-dihydro-3-hydroxy-2,2-dimethyl-2H-1-benzopyran-6-carbonitrile (2.40 g).

IR (CHCl$_3$, soln.): 3400, 2225, 1610, 1570 cm$^{-1}$
NMR (CDCl$_3$, δ): 1.22 (3H, s), 1.50 (3H, s), 2.41 (3H, br s), 3.34 (1H, d, J=9.7 Hz), 3.72 (1H, d, J=9.7 Hz), 6.83 (1H, d, J=8.5 Hz), 7.42 (1H, dd, J=8.5 Hz, 1.8 Hz), 7.79 (1H, d, J=1.8 Hz)
$[\alpha]_D^{23}$ = −79.2° (C=1, ethanol)

Preparation 7

N-Bromosuccinimide (6.408 g) was added to a solution of 2,2-dimethyl-2H-1-benzopyran-6-carbonitrile (5.55 g) and N-benzyloxycarbonyl-L-alanine (6.69 g) in chloroform (60 ml). After being stirred under reflux for 16 hours, the mixture was poured into saturated aqueous sodium bicarbonate and diluted with chloroform. The organic layer was separated, washed successively with 5% aqueous sodium thiosulfate, water, and brine, dried over magnesium sulfate, and evaporated in vacuo. The oily residue was dissolved in diisopropyl ether and allowed to stand at ambient temperature. The resulting precipitates were collected by filtration, washed with diisopropyl ether, and dried to give (3R,4S)-4-{(2S)-2-benzyloxycarbonylaminopropionyloxy}-3-bromo-3,4-dihydro-2,2-dimethyl-2H-1-benzopyran-6-carbonitrile (4.26 g).

mp: 137° to 138° C.

IR (Nujol): 3315, 2230, 1750, 1680 cm$^{-1}$

NMR (CDCl$_3$, δ): 1.50 (3H, s), 1.52 (3H, d, J=6 Hz), 1.61 (3H, s), 4.23 (1H, d, J=8 Hz), 4.44 (1H, quintet, J=6 Hz), 5.16 (2H, s), 5.33 (1H, b.d., J=6 Hz), 6.27 (1H, d, J=8 Hz), 6.91 (1H, d, J=8 Hz), 7.26–7.39 (5H, m), 7.49–7.54 (2H, m)

[α]$_D^{21}$: +69.9° (C=1, CHCl$_3$)

Preparation 8

A solution of sodium hydroxide (0.672 g) in water (16 ml) was added dropwise to a stirred solution of (3R,4S)-4-{(2S)-2-benzyloxycarbonylaminopropionyloxy}-3-bromo-3,4-dihydro-2,2-dimethyl-2H-1-benzopyran-6-carbonitrile (3.896 g) in 1,4-dioxane (24 ml). After being stirred at ambient temperature for 1 hour, the mixture was poured into ice-water and extracted with ethyl acetate. The extract was washed with water, dried over magnesium sulfate, and evaporated in vacuo. The crystalline residue was washed with isopropyl ether and dried to give (3S,4S)-3,4-epoxy-3,4-dihydro-2,2-dimethyl-2H-1-benzopyran-6-carbonitrile (1.401 g).

mp: 142.5° to 143.5° C.

IR (Nujol): 2230 cm$^{-1}$

NMR (CDCl$_3$, δ): 1.30 (3H, s), 1.60 (3H, s), 3.55 (1H, d, J=4 Hz), 3.92 (1H, d, J=4 Hz), 6.87 (1H, d, J=8 Hz), 7.53 (1H, dd, J=2, 8 Hz), 7.66 (1H, d, J=2 Hz)

[α]$_D^{21}$: 76.1° (C=1, CHCl$_3$)

Preparation 9

A solution of (3S,4S)-3,4-epoxy-3,4-dihydro-2,2-dimethyl-2H-1-benzopyran-6-carbonitrile (1.0 g) in ethanol (5 ml) and 28% ammonia water (10 ml) was stirred at room temperature for 4 days.

The reaction mixture was evaporated in vacuo to give (3S,4R)-4-amino-3,4-dihydro-3-hydroxy-2,2-dimethyl-2H-1-benzopyran-6-carbonitrile (1.1 g).

IR (CHCl$_3$): 3400, 2220, 1610, 1570 cm$^{-1}$

Preparation 10

To a suspension of 3-acetyl-4-hydroxybenzonitrile (10.48 g) and 3-pentanone (10.3 ml) in toluene (20 ml) was added pyrrolidine (2.7 ml) at ambient temperature. The reaction mixture was stirred overnight at the same temperature and for 3.5 hours under reflux, diluted with ethyl acetate, and then washed with water, 10% aqueous hydrochloric acid, saturated sodium bicarbonate solution and brine successively. The extract was dried over anhydrous magnesium sulfate and evaporated in vacuo. The residue was purified with silica gel column chromatography using a mixture of methylene chloride and n-hexane (1:10→1:1) as an eluent. The fractions containing the object compound were concentrated in vacuo and the residue was triturated to give 2,2-diethyl-3,4-dihydro-4-oxo-2H-1-benzopyran-6-carbonitrile (2.51 g).

mp: 69° to 70° C.

IR (Nujol): 2225, 1690 cm$^{-1}$

NMR (CDCl$_3$, δ): 0.95 (6H, t, J=7.4 Hz), 1.70–1.90 (4H, m), 2.78 (2H, s), 7.08 (1H, d, J=8.5 Hz), 7.69 (1H, dd, J=2.2, 8.5 Hz), 8.15 (1H, d, J=2.2 Hz)

MASS: 229, 200, 146

Preparation 11

To a solution of 2,2-diethyl-3,4-dihydro-4-oxo-2H-1-benzopyran-6-carbonitrile (2.29 g) in a mixture of methanol (23 ml) and tetrahydrofuran (5 ml) was added sodium borohydride (0.37 g) at ambient temperature. The reaction mixture was stirred for an hour at the same temperature and evaporated in vacuo. The residue was dissolved in ethyl acetate, and then washed with water and brine successively. The extract was dried over anhydrous magnesium sulfate, and evaporated in vacuo. The residue was purified with silica gel column chromatography using a mixture of methanol and methylene chloride (1:20) as an eluent to give 2,2-diethyl-3,4-dihydro-4-hydroxy-2H-1-benzopyran-6-carbonitrile (2.34 g).

IR (Film): 3400, 2220 cm$^{-1}$

NMR (CDCl$_3$, δ): 0.85–1.05 (6H, m), 1.45–1.95 (5H, m), 2.15–2.40 (2H, m), 4.75–4.90 (1H, m), 6.84 (1H, d, J=8.5 Hz), 7.42 (1H, dd, J=20, 8.5 Hz), 7.80 (1H, br s)

MASS: 231, 213, 201

Preparation 12

A mixture of 2,2-diethyl-3,4-dihydro-4-hydroxy-2H-1-benzopyran-6-carbonitrile (2.28 g) and p-toluenesulfonic acid hydrate (0.19 g) in toluene was refluxed for an hour and 20 minutes with azeotropic removal of the formed water. The reaction mixture was diluted with ethyl acetate, and then washed with water and brine successively. The extract was dried over anhydrous magnesium sulfate and evaporated in vacuo. The residue was purified with silica gel column chromatography using a mixture of methylene chloride and n-hexane (1:5) as an eluent to give 2,2-diethyl-2H-1-benzopyran-6-carbonitrile (1.47 g).

IR (Film): 2225, 1645 cm$^{-1}$

NMR (CDCl$_3$, δ): 0.93 (6H, t, J=7.4 Hz), 1.50–1.90 (4H, m), 5.54 (1H, d, J=10.2 Hz), 6.39 (1H, d, J=10.2 Hz), 6.77 (1H, d, J=8.4 Hz), 7.20 (1H, d, J=2.0 Hz), 7.35 (1H, dd, J=2.0, 8.4 Hz)

MASS: 213, 184, 169

Preparation 13

To a solution of 2,2-diethyl-2H-1-benzopyran-6-carbonitrile 41.44 g) in a mixture of dimethyl sulfoxide (3 ml) and water (0.14 g) was added N-bromosuccinimide (1.38 g) in one portion under water-cooling. The reaction mixture was stirred for 30 minutes at ambient temperature, poured into water, extracted with ethyl acetate, and then washed with water and brine successively. The extract was dried over anhydrous magnesium sulfate and evaporated in vacuo. The residue was triturated with diisopropyl ether to give trans-3-bromo-2,2-diethyl-3,4-dihydro-4-hydroxy-2H-1-benzopyran-6-carbonitrile (0.98 g).

mp: 105° to 106° C.

IR (Nujol): 3475, 2220 cm$^{-1}$

NMR (CDCl$_3$, δ): 0.92 (3H, t, J=7.4 Hz), 0.99 (3H, t, J=7.4 Hz), 1.65–2.20 (4H, m), 2.85 (1H, br s), 4.28 (1H, d, J=9.4 Hz), 5.00 (1H, d, J=9.4 Hz), 6.90 (1H, d, J=8.6 Hz), 7.48 (1H, dd, J=2, 8.6 Hz), 7.83 (1H, br s)

MASS: 311, 309, 282, 280, 212

Preparation 14

A mixture of trans-3-bromo-2,2-diethyl-3,4-dihydro-4-hydroxy-2H-1-benzopyran-6-carbonitrile (1.95 g) and potassium carbonate (1.74 g) in N,N-dimethylformamide (8 ml) was stirred overnight at ambient temperature. The reaction mixture was poured into water, extracted with ethyl acetate, and then washed with water and brine successively. The extract was dried over anhydrous magnesium sulfate, treated with active charcoal, and evaporated in vacuo. The residue was purified with silica gel column chromatography using a mixture of methylene chloride and n-hexane (1:2) as an eluent to give 3,4-epoxy-2,2-diethyl-3,4-dihydro-2H-1-benzopyran-6-carbonitrile (1.17 g).

IR (Film): 2220 cm$^{-1}$
NMR (CDCl$_3$, δ): 0.90 (3H, t, J=7.5 Hz), 1.09 (3H, t, J=7.6 Hz), 1.45–1.75 (2H, m), 1.75–2.10 (2H, m), 3.61 (1H, d, J=4.4 Hz), 3.88 (1H, d, J=4.4 Hz), 6.88 (1H, d, J=8.5 Hz), 7.52 (1H, dd, J=2, 8.5 Hz), 7.65 (1H, d, J=2 Hz)
MASS: 229, 201

EXAMPLE 1

To a suspension of 2-cyanoiminoimidazolidine (0.42 g) in dimethyl sulfoxide (12.5 ml) was added 60% sodium hydride (0.15 g) under water-cooling and the mixture was stirred at room temperature for 0.5 hours. 3,4-Epoxy-3,4-dihydro-2,2-dimethyl-2H-1-benzopyran-6-carbonitrile (0.50 g) was added portionwise thereto. After being stirred at room temperature overnight, the mixture was poured into ice-brine (50 ml) and extracted with ethyl acetate (50 ml). The extract was washed with brine, dried over anhydrous magnesium sulfate, and evaporated in vacuo. The residue was pulverized with chloroform and recrystallized from ethanol to give trans-4-(2-cyanoiminoimidazolidin-1-yl)-3,4-dihydro-3-hydroxy-2,2-dimethyl-2H-1-benzopyran-6-carbonitrile (0.15 mp: 245° to 248° C (dec.)
IR (Nujol): 3350, 3250, 2225, 2175, 1610 cm$^{-1}$
NMR (DMSO-d$_6$, δ): 1.17 (3H, s), 1.43 (3H, s), 2.99–3.57 (5H, m), 4.80 (1H, d, J=10 Hz), 5.77 (1H, d, J=5 Hz), 6.90 (1H, d, J=8 Hz), 7.37 (1H, br s), 7.58 (1H, dd, J=2.8 Hz), 7.99 (1H, br s)
MASS: 310 (M$^+$−1), 293 (M$^+$−H$_2$O), 278
Anal Calcd. for C$_{16}$H$_{17}$N$_5$O$_2$·½ C$_2$H$_5$OH: C 61.06, H 6.03, N 20.94; Found: C 60.92, H 6.08, N 20.99

EXAMPLE 2

A mixture of trans-4-(2-cyanoiminoimidazolidin-1-yl)-3,4-dihydro-3-hydroxy-2,2-dimethyl-2H-1-benzopyran-6-carbonitrile (0.62 g) and acetic anhydride (0.47 ml) in dry pyridine (3.1 ml) was stirred at room temperature for 3 days. The mixture was diluted with ethyl acetate (30 ml) and washed with 5% hydrochloric acid (20 ml×2), brine (20 ml), saturated aqueous sodium bicarbonate (20 ml) and brine (20 ml), successively. The organic layer was dried over anhydrous magnesium sulfate and evaporated in vacuo. The residue was subjected to column chromatography on silica gel (50 g) and eluted with a mixture of chloroform and methanol (50:1). The fractions containing the object compound were combined and concentrated under reduced pressure. The residue was recrystallized from a mixture of dichloromethane and n-hexane to give trans-3-acetoxy-4-(2-cyanoiminoimidazolidin-1-yl)-3,4-dihydro-2,2-dimethyl-2H-1-benzopyran-6-carbonitrile (0.44 g).

mp: 223° to 224° C. (dec.)
IR (Nujol): 3220 (shoulder), 3180, 2235, 2180, 1757, 1620 cm$^{-1}$
NMR (DMSO-d$_6$, δ): 1.28 (3H, s), 1.38 (3H, s), 2.08 (3H, s), 3.00–3.74 (4H, m), 5.13 (2H, s), 7.02 (1H, d, J=8 Hz), 7.61 (1H, d, J=2 Hz), 7.68 (1H, dd, J=2 Hz, 8 Hz), 8.12 (1H, br s)
MASS: 293 (M$^+$—CH$_3$COOH), 278 (M$^+$—CH$_3$COOH—CH$_3$)
Anal. Calcd. for C$_{18}$H$_{19}$N$_5$O$_3$: C 61.18, H 5.42, N 19.82; Found: C 60.60, H 5.44, N 19.55

EXAMPLE 3

To a suspension of trans-3-acetoxy-4-(2-cyanoiminoimidazolidin-1-yl)-3,4-dihydro-2,2-dimethyl-2H-1-benzopyran-6-carbonitrile (0.35 g) in toluene (7 ml) was added 1,8-diazabicyclo[5.4.0]undec-7-ene (0.19 ml) and the mixture was stirred under reflux for 2.5 hours. The solvent was evaporated in vacuo and the residue was dissolved in a mixture of ethyl acetate and water. The organic layer was separated, washed with brine, dried over anhydrous magnesium sulfate, and evaporated in vacuo. The residue was recrystallized from ethanol to give 4-(2-cyanoiminoimidazolidin-1-yl)-2,2-dimethyl-2H-1-benzopyran-6-carbonitrile (0.17 g).

mp: 249° to 252° C. (dec.)
IR (Nujol): 3215, 2230, 2175, 1657, 1611, 1275 cm$^{-1}$
NMR (DMSO-d$_6$, δ): 1.46 (6H, s), 3.40–4.00 (4H, m), 5.99 (1H, s), 6.94 (1H, d, J=8 Hz), 7.46 (1H, br s), 7.63 (1H, dd, J=2 Hz, 8 Hz), 8.33 (1H, br s)
MASS: 293 (M$^+$), 278
Anal. Calcd. for C$_{17}$H$_{17}$N$_5$O: C 65.52, H 5.15, N 23.88; Found: C 65.23, H 5.26, N 23.87

EXAMPLE 4

To a mixture of trans-4-(2-cyanoiminoimidazolidin-1-yl)-3,4-dihydro-3-hydroxy-2,2-dimethyl-2H-1-benzopyran-6-carbonitrile (0.50 g) and potassium carbonate (0.66 g) in N,N-dimethylformamide (5 ml) was added methyl iodide (0.30 ml). The reaction mixture was stirred at 80° C. for 5 hours, poured into water (50 ml) and extracted with ethyl acetate (50 ml). The organic layer was washed successively with aqueous sodium bisulfite (25 ml) and brine (25 ml), dried over magnesium sulfate, and then evaporated in vacuo. The residue was subjected to column chromatography on silica gel (15 g) and eluted with chloroform and then a mixture of chloroform and methanol (50:1). The fractions containing the object compound were combined and concentrated under reduced pressure. The residue was recrystallized from isopropyl alcohol to give trans-4-(2-cyanoimino-3-methylimidazolidin-1-yl)-3,4-dihydro-3-hydroxy-2,2-dimethyl-2H-1-benzopyran-6-carbonitrile (0.10 g).

mp : 243° to 246° C. (dec.)
IR (Nujol): 3335, 2225, 2170, 1608 cm$^{-1}$
NMR (DMSO-d$_6$, δ): 1.18 (3H, s), 1.43 (3H, s), 3.11 (3H, s), 3.38–3.84 (5H, m), 5.18 (1H, br d, J=10 Hz), 5.78 (1H, d, J=6 Hz), 6.91 (1H, d, J=8 Hz), 7.51 (1H, d, J=2 Hz), 7.60 (1H, dd, J=2, 8 Hz)
MASS: 325, 307, 292
Anal. Calcd. for C$_{17}$H$_{19}$N$_5$O$_2$: C 62.76, H 5.89, N 21.52; Found: C 62.26, H 5.93, N 20.88

EXAMPLE 5

To a solution of trans-4-(2-cyanoimino-3-methylimidazolidin-1-yl)-3,4-dihydro-3-hydroxy-2,2-dimethyl-2H-1-benzopyran-6-carbonitrile (0.95 g) in dry pyridine (9.5 ml) was added acetic anhydride (0.68 ml) at ambient temperature. The reaction mixture was stirred for 21 hours and 20 minutes at ambient temperature and then diluted with ethyl acetate (90 ml). The resultant solution was washed successively with 10% hydrochloric acid (50 ml, 30 ml), water (50 ml), saturated aqueous sodium bicarbonate (50 ml), dried over magnesium sulfate, and evaporated in vacuo. The residue was triturated with diisopropyl ether, and recrystallized from ethanol to give trans-3-acetoxy-4-(2- cyanoimino-3-methylimidazolidin-1-yl)-3,4-dihydro-2,2-dimethyl-2H-1-benzopyran-6-carbonitrile (0.57 g).

mp: 212° to 214° C. (dec.)

IR (Nujol): 2230, 2165, 1742, 1603 cm$^{-1}$

NMR (CDCl$_3$, δ): 1.33 (3H, s), 1.41 (3H, s), 2.14 (3H, s), 3.23 (3H, s), 2.93–3.67 (4H, m), 5.06 (1H, d, J=10 Hz), 5.61 (1H, d, J=10 Hz), 6.89 (1H, d, J=8 Hz), 7.33 (1H, d, J=2 Hz), 7.44 (1H, dd, J=2, 8 Hz)

MASS: 367, 307, 292

Anal. Calcd. for C$_{19}$H$_{21}$N$_5$O$_3$: C 62.11, H 5.76, N 19.06; Found: C 62.13, H 5.90, N 19.03

EXAMPLE 6

To a suspension of trans-3-acetoxy-4-(2-cyanoimino-3-methylimidazolidin-1-yl)-3,4-dihydro-2,2-dimethyl-2H-1-benzopyran-6-carbonitrile (0.45 g) in toluene (9 ml) was added 1,8-diazabicyclo[5.4.0]undec-7-ene (0.23 ml), and the reaction mixture was stirred at 100° C. for 2 hours and 40 minutes. The solvent was removed under reduced pressure. The residue was poured into water (30 ml) and then extracted with ethyl acetate (45 ml). The organic layer was washed with brine (30 ml), dried over magnesium sulfate and evaporated in vacuo. The residue was recrystallized from ethanol to give 4-(2-cyanoimino-3-methylimidazolidin-1-yl)-2,2-dimethyl-2H-1-benzopyran-6-carbonitrile (0.27 g).

mp: 222° to 225° C. (dec.)

IR (Nujol): 2225, 2170, 1655, 1605, 1280 cm$^{-1}$

NMR (CDCl$_3$, δ): 1.54 (6H, s), 2.99 (3H, s), 3.62 (4H, s), 5.74 (1H, s), 6.83 (1H, d, J=8 Hz), 7.34 (1H, d, J=2 Hz), 7.41 (1H, dd, J=2, 8 Hz)

MASS: 307 (M+), 292

Anal. Calcd. for C$_{17}$H$_{17}$N$_5$O: C 66.43, H 5.57, N 22.79; Found: C 66.74, H 5.69, N 22.67

EXAMPLE 7

A mixture of trans-4-amino-3,4-dihydro-3-hydroxy-2,2-dimethyl-2H-1-benzopyran-6-carbonitrile (2.18 g) and dimethyl N-cyanoimidodithiocarbonate [(CH$_3$S)$_2$C=N—CN] (1.54 g) in dry pyridine (11 ml) was stirred at 80° C. for 2.5 hours, and under reflux for 2.5 hours. The reaction mixture was diluted with ethyl acetate (40 ml) and washed with 5% hydrochloric acid (30 ml×2). The organic layer was washed successively with water (30 ml), saturated aqueous sodium bicarbonate (30 ml) and brine (30 ml), dried over magnesium sulfate, and evaporated in vacuo. The residue was subjected to column chromatography on silica gel (70 g) and eluted with chloroform and a mixture of chloroform and methanol (50:1 and then 20:1). The fractions containing the object compound were combined and concentrated under reduced pressure. The residue was triturated with diisopropyl ether. The crystals were recrystallized from ethanol to give trans-4-(3-cyano-2-methyl-1-isothioureido)-3,4-dihydro-3-hydroxy-2,2-dimethyl-2H-1-benzopyran-6-carbonitrile (2.01 g).

mp: 208° to 210° C. (dec.)

IR (Nujol): 3390, 3350, 2230, 2185, 1618, 1081 cm$^{-1}$

NMR (DMSO-d$_6$, δ): 1.16 (3H, s), 1.41 (3H, s), 2.62 (3H, s), 3.78 (1H, dd, J=6, 10 Hz), 5.04 (1H, br t, J=6 Hz), 5.86 (1H, d, J=6 Hz), 6.91 (1H, d, J=8 Hz), 7.47 (1H, d, J=2 Hz), 7.61 (1H, dd, J=2, 8 Hz), 8.53 (1H, br d, J=6 Hz)

MASS: 316, 298, 272, 268, 253

Anal. Calcd. for C$_{15}$H$_{16}$N$_4$O$_2$S: C 56.95, H 5.10, N 17.71; Found: C 56.93, H 5.14, N 17.46

EXAMPLE 8

The mixture of trans-4-(3-cyano-2-methyl-1-isothioureido)-3,4-dihydro-3-hydroxy-2,2-dimethyl-2H-1-benzopyran-6-carbonitrile (0.50 g) and 25% aqueous methylamine (10 ml) in ethanol (10 ml) was stirred under reflux for 1 hour and 10 minutes. The solvent was evaporated under reduced pressure. The residue was dissolved in ethyl acetate (30 ml), dried over magnesium sulfate and evaporated in vacuo. The residue was subjected to column chromatography on silica gel (10 g) and eluted with chloroform and then a mixture of chloroform and methanol (20:1). The fractions containing the object compound were combined and concentrated under reduced pressure. The residue was triturated with diisopropyl ether to give trans-4-(2-cyano-3-methylguanidino)-3,4-dihydro-3-hydroxy-2,2-dimethyl-2H-1-benzopyran-6-carbonitrile (0.38 g).

mp: 127° to 133° C. (dec.)

IR (Nujol): 3310 (br), 2220, 2160, 1605 cm$^{-1}$

NMR (DMSO-d$_6$, δ): 1.17 (3H, s), 1.40 (3H, s), 2.73 (3H, d, J=4 Hz), 3.69 (1H, dd, J=6, 9 Hz), 4.78 (1H, t, J=9 Hz), 5.72 (1H, d, J=6 Hz), 6.88 (1H, d, J=8 Hz), 7.00–7.33 (2H, m), 7.46 (1H, d, J=2 Hz), 7.58 (1H, dd, J=2, 8 Hz)

MASS: 299, 281, 266

EXAMPLE 9

The following compound was obtained according to a similar manner to that of Example 1.

trans-4-(2-Cyanoiminothiazolidin-3-yl)-3,4-dihydro-3-hydroxy-2,2-dimethyl-2H-1-benzopyran-6-carbonitrile.

mp: 262° to 267° C. (dec.)

IR (Nujol): 3280, 2225, 2190, 1610, 1077 cm$^{-1}$

NMR (DMSO-d$_6$, δ): 1.16 (3H, s), 1.44 (3H, s), 3.33–4.00 (5H, m), 5.21 (1H, br d, J=10 Hz), 5.98 (1H, d, J=6 Hz), 6.94 (1H, d, J=9 Hz), 7.47 (1H, br s), 7.63 (1H, dd, J=2, 9 Hz)

MASS: 328, 310, 295

EXAMPLE 10

To a suspension of trans-4-(2-cyanoiminothiazolidin-3-yl)-3,4-dihydro-3-hydroxy-2,2 TM dimethyl-2H-1-benzopyran-6-carbonitrile (0.21 g) in dry pyridine (2.1 ml) was added acetic anhydride (0.076 ml). The reaction mixture was stirred overnight at ambient temperature and then diluted with ethyl acetate (20 ml). The resultant solution was washed successively with 5% hydrochloric acid (20 ml×2), water (20 ml), saturated aqueous sodium bicarbonate (20 ml) and brine (20 ml), dried over anhydrous magnesium sulfate, acetoxy-4-(2-cyanoiminothiazolidin-3--yl)-3,4-dihydro-2,2-dimethyl-2H-1-benzopyran-6-carbonitrile, which was suspended in toluene (2 ml) and 1,8-diazabicyclo[5.4.0]undec-7-ene (0.10 ml) was added thereto. The reaction mixture was stirred for 1 hour at ° C. The solvent was removed under reduced pressure. The residue was recrystallized from 95% ethanol to give -(2-cyanoiminothiazolidin-3-yl)-2,2-dimethyl-2H-1-benzopyran-6-carbonitrile (0.11 g).

mp: 261° to 263° C. (dec.)

IR (Nujol): 2230, 2095, 1655 cm$^{-1}$

NMR (DMSO-d$_6$, δ): 1.43 (6H, s), 3.69 (2H, t, J=7 Hz), 4.09 (2H, t, J=7 Hz), 6.14 (1H, s), 6.94 (1H, d, J=8 Hz), 7.56 (1H, br s), 7.61 (1H, dd, J=2, 8 Hz)

MASS: 310, 295

Anal. Calcd. for C$_{16}$H$_{14}$N$_{4}$OS: C 61.92, H 4.55, N 18.05; Found: C 62.00, H 4.49, N 18.19

EXAMPLE 11

The following compound was obtained according to a similar manner to that of Example 4.

trans-4-(3-Butyl-2-cyanoiminoimidazolidin-1-yl)-3,4-dihydro-3-hydroxy-2,2-dimethyl-2H-1-benzopyran-6-carbonitrile mp: 202° to 203° C.

IR (Nujol): 3330, 2225, 2165, 1595, 1280, 1075 cm$^{-1}$

NMR (DMSO-d$_6$, δ): 0.93 (3H, t, J=6 Hz), 1.19 (3H, s), 1.43 (3H, s), 1.10–1.81 (4H, m), 2.87–3.93 (7H, m), 5.19 (1H, br d, J=10 Hz), 5.80 (1H, d, J=6 Hz), 6.92 (1H, d, J=9 Hz), 7.42 (1H, d, J=2 Hz), 7.61 (1H, dd, J=2, 9 Hz)

MASS: 367, 349, 334

Anal. Calcd. for C$_{20}$H$_{25}$N$_5$O$_2$: C 65.37, H 6.86, N 19.06; Found: C 65.74, H 6.92, N 18.70

EXAMPLE 12

The following compound was obtained according to a similar manner to that of Example 10.

4-(3-Butyl-2-cyanoiminoimidazolidin-1-yl)-2,2-dimethyl-2H-1-benzopyran-6-carbonitrile mp: 202° to 204° C.

IR (Nujol): 2230, 2175, 1650, 1607, 1280 cm$^{-1}$

NMR (DMSO-d$_6$, δ): 0.93 (3H, t, J=6 Hz), 1.48 (6H, s), 1.08–1.74 (4H, m), 3.30 (2H, t, J=7 Hz), 3 64 (4H, br s), 5.99 (1H, s), 6.89 (1H, d, J=8 Hz), 7.58 (1H, d, J=2 Hz), 7.61 (1H, dd, J=2, 8 Hz)

MASS: 349, 334

Anal. Calcd. for C$_{20}$H$_{23}$N$_5$O: C 68.75, H 6.63, N 20.04; Found: C 68.82, H 6.34, N 19.97

EXAMPLE 13

The following compound was obtained according to a similar manner to that of Example 8.

trans-4-(3-Butyl-2-cyanoguanidino)-3,4-dihydro-3-hydroxy-2,2-dimethyl-2H-1-benzopyran-6-carbonitrile mp: 105° to 110° C. (dec.)

IR (Nujol): 3325 (br), 2225, 2170, 1580 (br) cm$^{-1}$

NMR (DMSO-d$_6$, δ): 0.89 (3H, t, J=6 Hz), 1.16 (3H, s), 1.40 (3H, s), 1.03–1.70 (4H, m), 3.16 (2H, q, J=6 Hz), 3.68 (1H, dd, J=6, 9 Hz), 4.77 [1H, t, J=9 Hz), 5.70 (1H, d, J=6 Hz), 6.91 (1H, d, J=8 Hz), 6.98–7.27 (2H, m), 7.39 (1H, d, J=2 Hz), 7.67 (1H, dd, J=2, 8 Hz)

MASS: 341, 323, 308

EXAMPLE 14

The following compound was obtained according to a similar manner to that of Example 1.

trans-4-(2-Cyano-1,3-dimethylguanidino)-3,4-dihydro-3-hydroxy-2,2-dimethyl-2H-1-benzopyran-6-carbonitrile mp: 247° to 249° C. (dec.)

IR (Nujol): 3270, 3160 (br), 2225 (shoulder), 2185, 1600, 1070 cm$^{-1}$

NMR (DMSO-d$_6$, δ): 1.16 (3H, s), 1.42 (3H, s), 2.59 (3H, s), 2.99 (3H, s), 3.67 (1H, br d, J=10 Hz), 5.26 (1H, br d, J=10 Hz), 5.78 (1H, br s), 6.90 (1H, d, J=8 Hz), 7.20 (1H, br s), 7.43 (1H, d, J=2 Hz), 7.59 (1H, dd, J=2, 8 Hz)

MASS: 313, 295, 280

Anal. Calcd. for C$_{16}$H$_{19}$N$_5$O$_2$: 61.33, H 6.11, N 22.35; C 61.06, H 6.06, N 22.22

EXAMPLE 15

A mixture of trans-4-(3-cyano-2-methyl-1-isothioureido)-3,4-dihydro-3-hydroxy-2,2-dimethyl-2H-1-benzopyran-6-carbonitrile (4.90 g) and 50% aqueous dimethylamine (24.5 ml) was stirred at 80° C. for 2 hours and 20 minutes. The forming precipitate was collected by filtration and washed with water. The product was recrystallized from 25% aqueous ethanol (40 ml) to give trans-4-(2-cyano-3,3-dimethylguanidino)-° ,4-dihydro-3-hydroxy-2,2-dimethyl-2H-1-benzopyran-6-carbonitrile (3.30 G).

mp: 174° to 175° C. (dec.)

IR (Nujol): 3650, 3345, 3240, 3150, 3075, 2225, 2175, 1600, 1268, 1062 cm$^{-1}$ NMR (DMSO-d$_6$, δ): 1.13 (3H, s), 1.46 (3H, s), 3.01 (6H, s), 3.64 (1H, dd, J=5, 9 Hz), 4.96 (1H, t, J=9 Hz), 5.74 (1H, d, J=5 Hz), 6.88 (1H, d, J=8 Hz), 7.13 (1H, d, J=9 Hz), 7.54 (1H, dd, J=2, 8 Hz), 7.61 (1H, br s)

MASS: 313, 295, 280, 242

Anal. Calcd. for C$_{16}$H$_{19}$N$_5$O$_2$·H$_2$O: C 59.61, H 6.25, N 21.72, H$_2$O 2.79; Found: C 59.79, H 6.32, N 21.70, H$_2$O 2.19

EXAMPLE 16

The following compounds were obtained according to a similar manner to that of Example 15.

(1) trans-4-{2-Cyano-3-methylguanidino)-3,4-dihydro-3-hydroxy-2,2-dimethyl-2H-1-benzopyran-6-carbonitrile mp: 218° to 221° C.

IR (Nujol): 3625, 3470, 3415, 3345, 3275, 3170, 2230, 2180, 1605, 1277, 1090, 1069 cm$^{-1}$ NMR (DMSO-d$_6$, δ): 1.13 (3H, s), 1.40 (3H, s), 2.76 (3H, d, J=5 Hz), 3.71 (1H, dd, J=5, 9 Hz), 4.78 (1H, t, J=9 Hz), 5.71 (1H, d, J=5 Hz), 6.88 [1H, d, J=8 Hz), 7.00–7.33 (2H, m), 7.47 (1H, br s), 7.56 (1H, dd, J=2, 8 Hz)

MASS: 299, 281, 266

(2) trans-4-(2-Cyano-3-ethylguanidino)-3,4-dihydro-3-hydroxy-2,2-dimethyl-2H-1-benzopyran-6-carbonitrile mp: 165° to 166° C.

IR (Nujol): 3540, 3430, 3350, 3240, 3130, 2220, 2148, 1580, 1262, 1060 cm$^{-1}$ NMR (DMSO-d , δ): 1.09 (3H, t, J=7 Hz), 1.16 (3H, s), 1.40 (3H, s), 3.16 (2H, q, J=7 Hz), 3.71 (1H, dd, J=6, 9 Hz), 4.79 (1H, t, J=9 Hz), 5.73 (1H, d, J=6 Hz), 6.89 (1H, d, J=8 Hz), 7.00–7.29 (2H, m), 7.42 (1H, br s), 7.58 (1H, dd, J=2, 8 Hz)

MASS: 313, 295, 280, 242

Anal. Calcd. for C$_{16}$H$_{19}$N$_5$O$_2$·H$_2$O; C 57.99, H 6.39, N 21.13, H$_2$O 5.75; Found: C 57.58, H 6.41, N 21.05, H20 6.01

(3) trans-4-(2-Cyano-3-isopropylguanidino)-3,4-dihydro-3-hydroxy-2,2-dimethyl-2H-1-benzopyran-6-carbonitrile IR (Nujol): 3300 (br), 2225, 2165, 1575 (br), 1262, 1068 cm$^{-1}$ NMR (DMSO-d$_6$, δ): 1.17 (6H, d, J=7 Hz), 1.17 (3H, s), 1.40 (3H, s), 3.69 (1H, dd, J=6, 9 Hz), 3.67–4.10 (1H, m), 4.79 (1H, t, J=9 Hz), 5.78 (1H, d, J=6 Hz), 6.78 (1H, d, J=7 Hz), 6.89 (1H, d, J=8 Hz), 7.15 (1H, d, J=9 Hz}, 7.41 (1H, br s), 7.58 (1H, dd, J=2, 8 Hz)

(4) trans-4-(2-Cyanoguanidino)-3,4-dihydro-3-hydroxy-2,2-dimethyl-2H-1-benzopyran-6-carbonitrile mp: 238° to 239° C. (dec.)

IR (Nujol): 3455, 3385, 3345, 3250, 2190, 1630, 1058 cm$^{-1}$

NMR (DMSO-d$_6$, δ): 1.17 (3H, s), 1.39 (3H, s), 3.55 (1H, dd, J=6, 9 Hz), 4.66 (1H, t, J=9 Hz), 5.69 (1H, d, J=6 Hz), 6.83 (2H, br s), 6.86 (1H, d, J=8 Hz), 7.18 (1H, d, J=9 Hz), 7.42 (1H, br s), 7.57 (1H, dd, J=2, 8 Hz)

MASS: 267, 252

Anal. Calcd. for C$_{14}$H$_{15}$N$_5$O$_2$: C 58.94, H 5.30, N 24.55; Found: C 58.73, H 5.41, N 24.08

(5) trans-4-[[(Cyanoimino)(1-pyrrolidinyl)methyl]amino]-3,4-dihydro-3-hydroxy-2,2-dimethyl-2H-1-benzopyran-6carbonitrile mp: 253° to 255° C. (dec.)

IR (Nujol): 3455, 3385, 3345, 3250, 2190, 1630, 1058 cm$^{-1}$

NMR (DMSO-d$_6$, δ): 1.17 (3H, s), 1.39 (3H, s), 1.67–2.00 (4H, m), 3.37–3.77 (5H, m), 4.97 (1H, t, J=9 Hz), 5.69 (1H, d, J=6 Hz), 6.60–7.00 (2H, m), 7.43–7.68 (2H, m)

MASS: 339, 321, 306, 268

Anal. Calcd. for C$_{18}$H$_{21}$N$_5$O$_2$: C 63.70, H 6.24, N 20.63; Found: C 63.30, H 6.37, N 19.98

(6) trans-4-[[(Cyanoimino)(morpholino)methyl]amino]-3,4-dihydro-3-hydroxy-2,2-dimethyl-2H-1-benzopyran-6-carbonitrile mp: 218° to 221° C. (dec.)

IR (Nujol): 3340, 2225, 2175, 1605 cm$^{-1}$

NMR (DMSO-d$_6$, δ): 1.16 (3H, s), 1.41 (3 H, s), 3.33–3.81 (9H, m), 4.94 (1H, t, J=9 Hz), 5.80 (1H, d, J=6 Hz), 6.90 (1H, d, J=8 Hz), 7.44 (1H, d, J=9 Hz), 7.59 (1H, dd, J=2, 8 Hz), 7.68 (1H, br s)

MASS: 355, 337, 322, 284

Anal. Calcd. for C$_{18}$H$_{21}$N$_5$O$_3$: C 60.83, H 5.96, N 19.71; Found: C 60.75, H 5.92, N 19.60

(7) trans-4-[[(Cyanoimino)(4-methyl-1-piperazinyl)methyl]amino]-3,4-dihydro-3-hydroxy-2,2-dimethyl-2H-1-benzopyran-6-carbonitrile mp: 211° to 212° C. (dec.)

IR (Nujol): 3220, 3120, 2225, 2155, 1610, 1284, 1080 cm$^{-1}$

NMR (DMSO-d$_6$, δ): 1.16 (3H, s), 1.41 (3H, s), 2.19 (3H, s), 2.26–2.43 (4H, m), 3.37–3.78 5H, m), 4.90 (1H, br t, J=9 Hz), 5.78 (1H, d, J=6 Hz), 6.91 (1H, d, J=9 Hz), 7.39 (1H, d, J=9 Hz), 7.58 (1H, dd, J=2, 9 Hz), 7.64 (1H, br s)

MASS: 368, 350, 339, 335, 325, 312, 298

(8) trans-4-[[(Cyanoimino)(piperidino)methyl]amino]-3,4-dihydro-3-hydroxy-2,2-dimethyl-2H-1-benzopyran-6-carbonitrile mp: 204° to 206° C.

IR (Nujol): 3340, 2220, 2175, 1570 cm$^{-1}$

NMR (DMSO-d$_6$, δ): 1.14 (3H, s), 1.40 (3H, s), 1.56 (6H, br s), 3.46 (4H, br s), 3.62 (1H, dd, J=6, 9 Hz), 4.88 (1H, t, J=9 Hz), 5.71 (1H, d, J=6 Hz), 6.89 (1H, d, J=9 Hz), 7.39 (1H, d, J=9 Hz), 7.57 (1H, dd, J=2, 9 Hz), 7.62 (1H, br s)

MASS: 353, 335, 320, 311, 282, 240

Anal. Calcd. for C$_{19}$H$_{23}$N$_5$O$_2$: C 64.57, H 6.56, N 19.82; Found: C 64.37, H 6.70, N 19.68

EXAMPLE 17

A mixture of trans-4-(3-cyano-2-methyl-1-isothioureido)-3,4-dihydro-3-hydroxy-2,2-dimethyl-2H-1-benzopyran-6-carbonitrile (0.48 g) and triethylamine (0.635 ml) in ethanol (5.0 ml) was stirred under reflux for 7 hours. The solvent was removed under reduced pressure. The residue was extracted with ethyl acetate (15 ml), and washed successively with 5% hydrochloric acid (15 ml) and saturated aqueous solution of sodium chloride (15 ml). The organic solution was dried over anhydrous magnesium sulfate and evaporated in vacuo. The residue was subjected to a column chromatography on silica gel (17 g), eluting with a mixture of methanol and chloroform (1:50 V/V). The fractions containing the object compound were combined and concentrated under reduced pressure. The residue was recrystallized from a mixture of ethanol 1.5 ml) and n-hexane (3 ml) to give trans-4-(3-cyano-2-ethyl-1-isoureido)-3,4-dihydro-3-hydroxy-2,2-dimethyl-2H-1-benzopyran-6-carbonitrile (0.22 g).

mp: 193° to 196° C.

IR (Nujol): 3440, 3300, 3160, 2220 (shoulder), 1605 (br), 1260, 1070, 1040 cm$^{-1}$ NMR (DMSO-d$_6$, δ): 1.14 (3H, s), 1.22 (3H, t, J=7Hz), 1.40 (3H, s), 3.71 (1H, dd, J=5, 10Hz), 4.25 (2H, q, J=7Hz), 4.62 (1H, br t, J=9Hz), 5.85 (1H, d, J=5Hz), 6.88 (1H, d, J=9Hz), 7.44–7.80 (2H, m), 8.17–8.63 (1H, m)

MASS: 314, 296, 281, 243

Anal Calcd. for C$_{16}$H$_{18}$H$_4$O$_3$: C 61.14, H 5.77, N 17.82; Found: C 61.27, H 5.82, N 17.74

EXAMPLE 18

A mixture of trans-4-(2-cyanoiminoimidazolidin-1-yl)-3,4-dihydro-3-hydroxy-2,2-dimethyl-2H-1-benzopyran-6carbonitrile (0.78 g), ethyl bromide (1.08 g) and potassium carbonate (1.38 g) in N,N-dimethylformamide (7.8 ml) was heated for 3 hours at 63° C. The reaction mixture was poured into ice-water (50 ml), and extracted with ethyl acetate. The extract was washed with water, and dried over anhydrous magnesium sulfate. The solvent was removed under reduced pressure. The residue was recrystallized from ethanol to give trans-4-(2-cyanoimino-3-ethylimidazolidin-1-yl)-3,4-dihydro-3-hydroxy-2,2-dimethyl-2H-1-benzopyran-6-carbonitrile (0.58 g).

mp: 231° to 233° C.

IR (Nujol): 3240, 3220, 2170, 1590, 1525 cm$^{-1}$

NMR (DMSO-d$_6$, δ): 1.19 (3H, t, J=7 Hz), 1.20 (3H, s), 1.45 (3H, s), 2.80–3.90 (7H, m), 5.21 (1H, d, J=10 Hz), 5.80 (1H, d, J=6 Hz), 6.91 (1H, d, J=9 Hz), 7.44 (1H, d, J=2 Hz), 7.59 (1H, dd, J=2, 9 Hz)

MASS: 339, 321, 306, 268

Anal. Calcd. for C$_{18}$H$_{21}$N$_5$O$_2$: C 63.70, H 6.24, N 20.63; Found: C 63.75, H 6.35, N 20.52

EXAMPLE 19

The following compound was obtained according to a similar manner to that of Example 18.

trans-4-(2-Cyanoimino-3-isopropylimidazolidin-1-yl)-3,4-dihydro-3-hydroxy-2,2-dimethyl-2H-1-benzopyran-6-carbonitrile mp: 263° to 265° C. (dec.)

IR (Nujol): 3290, 2230, 2180, 1600 cm$^{-1}$

NMR (DMSO-d$_6$, δ): 1.18 (3H, d, J=6.6 Hz), 1.19 (3H, s), 1.22 (3H, d, J=6.6 Hz), 1.46 (3H, s), 3.20–3.60 (4H, m), 4.61 (1H, septet, J=6.6 Hz), 4.73 (1H, br s), 5.36 (1H, br s), 5.90 (1H, br s), 6.97 (1H, d, J=8.6 Hz), 7.44 (1H, br s), 7.65 (1H, dd, J=2.0, 8.6 Hz)

MASS: 353, 335, 320, 282

Anal. Calcd. for C$_{19}$H$_{23}$N$_5$O$_2$: C 64.57, H 6.56, N 19.82; Found: C 64.74, H 6.61, N 19.88

EXAMPLE 20

60% Dispersion of sodium hydride (0.40 g) in mineral oil was added in small portion at ambient temperature to a solution of 2-cyanoimino-1-ethylimidazolidine (1.38 g) in dimethyl sulfoxide (15 ml). The reaction mixture was stirred for 30 minutes at the same temperature, and 3,4-epoxy-3,4-dihydro-2,2-dimethyl-2H-1-benzopyran-6-carbonitrile (1.01 g) was added thereto. The reaction mixture was stirred overnight at the same temperature, heated for 1.5 hours at 40° C., and then poured into ice-water (50 ml). The forming precipitate was collected by filtration, and washed with water. The product was recrystallized from ethanol to give 4-(2-cyanoimino-3-ethylimidazolidin-1-yl)-2,2-dimethyl-2H-1-benzopyran-6-carbonitrile (0.36 g).

mp: 197° to 199° C.

IR (Nujol): 2225, 2180, 1655, 1610, 1280 cm$^{-1}$

NMR (DMSO-d$_6$, δ): 1.13 (3H, t, J=7 Hz), 1.50 (6H, s), 3.36 (2H, quartet, J=7 Hz), 3.66 (4H, s), 6.01 (1H, s), 6.92 (1H, d, J=9 Hz), 7.60 (1H, dd, J=2, 9 Hz), 7.62 (1H, d, J=2 Hz)

MASS: 321, 306

Anal. Calcd. for C$_{18}$H$_{19}$N$_5$O: C 67.27, H 5.96, N 21.79; Found: C 67.25, H 5.96, N 21.67

EXAMPLE 21

60% Dispersion of sodium hydride (0.48 g) in mineral oil was added in small portion at ambient temperature to a solution of 2-cyanoiminohexahydropyrimidine (1.49 g) in dimethyl sulfoxide (18 ml). The reaction mixture was stirred at the same temperature for 30 minutes, and 3,4-epoxy-3,4-dihydro-2,2-dimethyl-2H-1-benzopyran-6carbonitrile (1.21 g) was added thereto. The reaction mixture was stirred overnight at ambient temperature and poured into ice-water (90 ml). The forming precipitate was collected by filtration and washed with water. The product was recrystallized from ethanol to give trans-4-(2-cyanoiminohexahydroxypyrimidin-1-yl)-3,4-dihydro-3-hydroxy-2,2-dimethyl-2H-1-benzopyran-6-carbonitrile (1.12 g).

mp: 253° to 255° C. (dec.)

IR (Nujol): 3360, 2220, 2165, 1580, 1545 cm$^{-1}$

NMR (DMSO-d$_6$, δ): 1.17 (3H, s), 1.45 (3H, s), 1.60–2.30 (2H, m), 2.60–3.50 (4H, m), 3.73 (1H, dd, J=5, 10 Hz), 5.57 (1H, d, J=10 Hz), 5.73 (1H, d, J=5 Hz), 6.93 (1H, d, J=9 Hz), 7.38 (1H, d, J=2 Hz), 7.57 (1H, br s), 7.59 (1H, dd, J=2, 9 Hz)

MASS: 325, 307, 292

Anal. Calcd. for C$_{17}$H$_{17}$N$_5$O$_2$: C 62.76, H 5.89, N 21.52; Found: C 63.24, H 5.95, N 21.09

EXAMPLE 22

A mixture of trans-4-(2-cyanoiminohexahydropyrimidin-1-yl)-3,4-dihydro-3-hydroxy-2,2-dimethyl-2H-1-benzopyran-6-carbonitrile (651 mg) and acetic anhydride (0.76 ml) in pyridine (2 ml) was stirred for 7 days at room temperature. The mixture was concentrated under reduced pressure, and the residue was dissolved in ethyl acetate, washed twice with water and dried over anhydrous magnesium sulfate. The solvent was evaporated in vacuo and the residue was pulverized with diisopropyl ether to give trans-3-acetoxy-4-(2-cyanoiminohexahydropyrimidin-1-yl)-3,4-dihydro-2,2-dimethyl-2H-1-benzopyran-6carbonitrile (0.76 g).

mp: 245° to 246° C.

IR (Nujol): 3350, 3260, 2230, 2180, 1750, 1590, 1545 cm$^{-1}$

NMR (DMSO-d$_6$, δ): 1.26 (3H, s), 1.38 (3H, s), 1.75 (2H, m), 2.09 (3H, s), 2.6–3.3 (4H, m), 5.13 (1H, d, J=10 Hz), 5.90 (1H, d, J=10 Hz), 7.00 (1H, d, J=9 Hz), 7.5–7.8 (2H, m)

MASS: 367, 324, 307, 292

Anal. Calcd. for C$_{19}$H$_{21}$N$_5$O$_3$·C$_2$H$_6$O: C 61.00, H 6.58, N 16.94; Found: C 60.97, H 6.44, N 16.91

EXAMPLE 23

A mixture of trans-3-acetoxy-4-(2-cyanoiminohexahydropyrimidin-1-yl)-3,4-dihydro-2,2-dimethyl-2H-1-benzopyran-6-carbonitrile (0.37 g) and 1,8-diazabicyclo[5.4.0]undec-7-ene (0.46 g) in toluene (15 ml) was stirred at 100° C. for 24 hours. The mixture was concentrated under reduced pressure. The residue was suspended in water, collected by filtration, and recrystallized from ethanol to give 4-(2-cyanoiminohexahydropyrimidin-1-yl)-2-2-dimethyl-2H-1-benzopyran-6-carbonitrile (0.24 g).

mp: 282° to 285° C. (dec.)

IR (Nujol): 3250, 2220, 2170, 1665, 1590, 1550 cm$^{-1}$

NMR (DMSO-d$_6$, δ): 1.40 (3H, s), 1.46 (3H, s), 1.75–2.25 (2H, m), 3.15–3- 6 (4H, m), 5.91 (1H, s), 6.91 (1H, d, J=9 Hz), 7.35 (1H, d, J=2 Hz), 7.56 (1H, dd, J=9 Hz, 2 Hz), 7.73 (1H, br s)

MASS: 307, 292

Anal. Calcd. for C$_{17}$H$_{17}$N$_5$O: C 66.43, H 5.57, N 22.79; Found C 66.53, H 5.81, N 22.80

EXAMPLE 24

The following compound was obtained according to a similar manner to that of Example 21.

trans-4-(2-Cyanoimino-3-methylhexahydropyrimidin-1-yl)-3,4-dihydro-3-hydroxy-2,2-dimethyl-2H-1-benzopyran-6-carbonitrile mp: 252° to 254° C.

IR (Nujol): 3240, 2225, 2170, 1610, 156, 1520 cm$^{-1}$

NMR (DMSO-d$_6$, δ): 1.17 (3H, s), 1.45 (3H, s,, 1.70–2.30 (2H, m), 2.70–3.60 (7H, m), 3.70 (1H, dd, J=6, 10 Hz), 5.80 (1H, d, J=10 Hz), 5.83 (1H, d, J=6 Hz), 7.02 (1H, d, J=8 Hz), 7.50–7.80 (2H, m)

MASS: 339, 338, 322, 306, 268

Anal. Calcd. for C$_{18}$H$_{21}$N$_5$O$_2$: C 63.70, H 6.24, N 20.63; Found: C 63.95, H 6.37, N 20.67

EXAMPLE 25

The following compound was obtained according to a similar manner to that of Example 18.

4-(2-Cyanoimino-3-methylhexahydropyrimidin-1-yl)-2,2-dimethyl-2H-1-benzopyran-6-carbonitrile mp: 212° to 214° C.

IR (Nujol): 2210, 2150, 1650, 1570 cm$^{-1}$

NMR (DMSO-d$_6$, δ): 1.46 (3H, s), 1.48 (3H, s), 2.00 (2H, m), 3.02 (3H, s), 2.90–3.70 (4H, m), 5.83 (1H, s), 6.90 (1H, d, J=9 Hz), 7.53 (1H, br s), 7.58 (1H, dd, J=2, 9 Hz)

MASS: 321, 306

Anal. Calcd. for C$_{18}$H$_{19}$N$_5$O: C 67.27, H 5.96, N 21.79; Found: C 67.01, H 5.99, N 21.89

EXAMPLE 26

A mixture of 3,4-epoxy-3,4-dihydro-2,2-dimethyl-2H-1-benzopyran-6-carbonitrile (0.51 g), 2-cyanoiminothiazolidine (0.64 g) and pyridine (4.1 ml) was heated at 100° C. for 1.5 hours. Pyridine was removed under reduced pressure. The residue was diluted with ethyl acetate (20 ml). The solution was washed with water (20 ml and 15 ml), 5% aqueous hydrochloric acid (15 ml×2) and saturated aqueous sodium chloride (15 ml) successively, treated with charcoal, and then dried over anhydrous magnesium sulfate. The solvent was evaporated in vacuo, and the residue was triturated with ethyl acetate, to give trans-4-(2-cyanoiminothiazolidin-3-yl)-

3,4-dihydro-3-hydroxy-2,2-dimethyl-2H-1-benzopyran-6-carbonitrile (0.47 g).

IR (Nujol): 3280, 2225, 2190, 1610, 1077 cm

EXAMPLE 27

A mixture of 3,4-epoxy-3,4-dihydro-2,2-dimethyl-2H-1-benzopyran-6-carbonitrile (0.51 g), 2-cyanoiminothiazolidine (0.64 g), and triethylamine (4.1 ml) was heated at 100° C. for 5 hours. Triethylamine was removed under reduced pressure. To the residue was added a mixture of ethyl acetate (15 ml) and water (15 ml), and the mixture was stirred for 30 minutes. The precipitate was collected by filtration and washed with ethyl acetate to give trans-4-(2-cyanoiminothiazolidin-3-yl)-3,4-dihydro-3-hydroxy-2,2-dimethyl-2H-1-benzopyran-6-carbonitrile (0.60 g).

IR (Nujol): 3280, 2225, 2190, 1610, 1077 cm$^{-1}$

EXAMPLE 28

To a solution of trans-4-(2-cyanoiminothiazolidin-3-yl)-3,4-dihydro-3-hydroxy-2,2-dimethyl-2H-1-benzopyran-6-carbonitrile (1.31 g) in dry pyridine (6.55 ml) was added l-menthoxyacetyl chloride (1.86 g) under ice-cooling. The reaction mixture was stirred overnight at ambient temperature, diluted with ethyl acetate (50 ml), and washed successively with 5% aqueous hydrochloric acid (30 ml×2) and brine (30 ml×2). The ethyl acetate layer was treated with activated charcoal, dried over anhydrous magnesium sulfate, and evaporated in vacuo. The residue (3 g) was subjected to column chromatography or silica gel (150 g) and eluted with a mixture of ethyl acetate and n-hexane (1:4→1:1) to give two diastereomers, that is, crude A-isomer (0.85 g) having lower polarity and crude B-isomer (0.60 g) having higher polarity. Crude A-isomer was recrystallized from a mixture of ethyl acetate and n-hexane (1:3) to give white needle of (3S,4R)-4-(2-cyanoiminothiazolidin-3-yl)-3,4-dihydro-3-(l-menthoxyacetoxy)-2,2-dimethyl-2H-1-benzopyran-6-carbonitrile (0.57 g). Similarly, crude B-isomer was recrystallized from a mixture of ethyl acetate and n-hexane (1:4) to give (3R,4S)-4-(2-cyanoiminothiazolidin-3-yl)-3,4-dihydro-3-(l-menthoxyacetoxy)-2,2-dimethyl-2H-1-benzopyran-6-carbonitrile (0.41 g) as another enantiomer. A-isomer mp: 170°–171° C.

IR (Nujol): 2230, 2175, 1760 cm$^{-1}$

NMR (CDCl$_3$, δ): 0.74–1.29 (13H, m), 1.33 (3H, s), 1.44 [3H, s], 1.50–1.78 (3H, s), 1.91–2.47 (2H, m), 3.00–4.41 (7H, m), 5.19 (1H,, d, J=10 Hz), 5.63 (1H, d, J=10 Hz), 6.96 (1H, d, J=8 Hz), 7.26 (1H, br s), 7.46 (1H, br d, 8 Hz)

MASS: 524, 509

Anal. Calcd. for C$_{28}$H$_{36}$N$_4$O$_4$S: C 64.10, H 6.92, N 10.68; Found: C 64.08, H 6.79, N 10.62

$[α]_D^{23.2}$: −3.2° (C=0.5, CHCl$_3$)

B-isomer mp: 157° C.

IR (Nujol): 2225, 2180, 1760 cm$^{-1}$

NMR (CDCl$_3$, δ): 0.73–1.32 (13H, m), 1.33 (3H, s), 1.43 (3H, s), 1.51–1.78 (3H, m), 1.88–2.43 (2H, m), 2.97–4.10 (6H, m), 4.14 (2H, s), 5.19 (1H, d, J=10 Hz), 5.64 (1H, d, J=10 Hz), 6.94 (1H, d, J=8 Hz), 7.23 (1H, br s), 7.51 (1H, br d, J=8 Hz)

MASS: 524

Anal. Calcd. for C$_{28}$H$_{36}$N$_4$OS: C 64.10, H 6.92, N 10.68; Found; C 63.73, H 6.95, N 10.54

$[α]_D^{23.2}$: −66.0° (C=0.5, CHCl$_3$)

EXAMPLE 29

To a solution of (3S,4R)-4-(2-cyanoiminothiazolidin-3-yl)-3,4-dihydro-3-(l-menthoxyacetoxy)-2,2-dimethyl-2H-1-benzopyran-6-carbonitrile (0.40 g) in methanol (8.0 ml) was added about 50% aqueous dimethylamine (0.11 ml) at ambient temperature. The reaction mixture was stirred at ambient temperature for 5 hours, and evaporated in vacuo. The residue was dissolved in a mixture of ethyl acetate (4 ml) and water (4 ml), and the organic layer was separated, washed with brine, dried over anhydrous magnesium sulfate and then evaporated in vacuo. The residue was triturated with ethyl acetate to give (3S,4R)-4-(2-cyanoiminothiazolidin-3-yl)-3,4-dihydro-3-hydroxy-2,2-dimethyl-2H-1-benzopyran-6-carbonitrile (0.16 g).

mp: 272°–274° .C (dec.)

IR (Nujol): 3300, 2215, 2180, 1080 cm$^{-1}$

NMR (DMSO-d$_6$, δ): 1.17 (3H, s), 1.43 (3H, s), 3.33–4.00 (5H, m), 5.19 (1H, br d, J=10 Hz), 5.94 (1H, d, J=5 Hz), 6.92 (1H, d, J=8 Hz), 7.40–7.77 (2H, m)

MASS: 328, 310, 295

$[α]_D^{22.4}$: −76.6° (C=0.5, methanol)

EXAMPLE 30

The following compound was obtained according to a similar manner to that of Example 29.

(3R,4S)-4-(2-Cyanoiminothiazolidin-3-yl)-3,4-dihydro-3-hydroxy-2,2-dimethyl-2H-1-benzopyran-6-carbonitrile mp 270°–271° C. (dec.)

IR (Nujol): 3300, 2210, 2180, 1078 cm$^{-1}$

NMR (DMSO-d$_6$, δ): 1.17 (3H, s), 1.43 (3H, s), 3.33-° 4.00 (5H, m), 5.20 (1H, br d, J=10 Hz), 5.96 (1H, d, J=5 Hz), 6.93 (1H, d, J=8 Hz), 7.39–7.72 (2H, m)

MASS: 328, 310, 295

$[α]_D^{22.4}$: +75.3° (C=0.3, methanol)

EXAMPLE 31

A solution of (3S,4R)-4-amino-3,4-dihydro-3-hydroxy-2,2-dimethyl-2H-1-benzopyran-6-carbonitrile (15.00 g) and dimethyl N-cyanoimidodithiocarbonate [(CH$_3$S)$_2$C=N—CN] (10.05 g) in pyridine (75 ml) was stirred at 80° C. for 10 hours, and then concentrated in vacuo. The residue was dissolved in ethyl acetate, and washed with 5% hydrochloric acid, brine, saturated aqueous sodium bicarbonate solution and brine, successively. The organic layer was dried over anhydrous magnesium sulfate and concentrated in vacuo. The residue was subjected to column chromatography on silica gel (300 g) and eluted with a mixture of chloroform and methanol (20:1). The fractions containing the object compound were combined and concentrated in vacuo to give (3S,4R)-4-(3-cyano-2-methyl-1-isothioureido)-3,4-dihydro-3-hydroxy-2,2-dimethyl-2H-1-benzopyran-6-carbonitrile (16.3 g).

mp: 193° to 194° C. (dec.)

IR (Nujol): 3490, 3410, 3220, 2240, 2200, 1530 cm$^{-1}$

NMR (DMSO-d$_6$, δ): 1.18 (3H, s), 1.44 (3H, s), 2.66 [3H, s], 3.82 (1H, dd, J=9.6 Hz, 5.7 Hz), 5.09 (1H, br t, J=8.5 Hz), 7.54 (1H, br s), 7.65 (1H, dd, J=8.5 Hz, 2 Hz), 8.60 (1H, d, J=7.8 Hz)

$[α]_D^{23}$: −202.40° (C=1, ethanol)

EXAMPLE 32

A mixture of (3S,4R)-4-(3-cyano-2-methyl-1-isothioureido)-3,4-dihydro-3-hydroxy-2,2-dimethyl-2H-1-benzopyran-6-carbonitrile (16.3 g) and 50% aqueous dimethylamine solution (81.5 ml) was stirred under reflux for 1.5 hours to form white precipitates. These precipitates were collected by filtration, washed with cold water, and recrystallized from ethanol to give (3S,4R)-4-(2-cyano-3,3-dimethylguanidino)-3,4-dihydro-3-hydroxy-2,2-dimethyl-2H-1-benzopyran-6-carbonitrile (12.05 g).

mp: 224° to 226° C. (dec.)

IR (Nujol): 3380, 3270, 2220, 2190, 1610, 1590, 1530 cm$^{-1}$

NMR (DMSO-d$_6$, δ): 1.15 (3H, s), 1.41 (3H, s), 3.03 (6H, s), 3.65 (1H, dd, J=9 Hz, 6 Hz), 4.97 (1H, t, J=9 Hz), 5.77 (1H, d, J=6 Hz), 6.90 (1H, d, J=8 Hz), 7.15 (1H, d, J=9 Hz), 7.5.-7.8 (2H, m)

$[α]_D^{20}$: −310.7° (C=1.0, methanol)

EXAMPLE 33

A solution of (3R,4S)-4-amino-3,4-dihydro-3-hydroxy-2,2-dimethyl-2H-1-benzopyran-6-carbonitrile (2.40 g) and dimethyl N-cyanoimidodithiocarbonate [(CH$_2$C=C—N—] (1.61 g) in pyridine (12 ml) was stirred at 80° C. for 10 hours, and then concentrated in vacuo. The residue was dissolved in ethyl acetate and washed with 5% aqueous hydrochloric acid, and brine. The organic layer was dried over anhydrous magnesium sulfate and concentrated in vacuo. The residue was subjected to column chromatography on silica gel (48 g) and eluted with a mixture of chloroform and methanol (20:1). The fractions containing the object compound were combined and concentrated in vacuo to give (3R,4S)-4-(3-cyano-2-methyl-1-isothioureido)-3,4-dihydro-3-hydroxy-2,2-dimethyl-2H-1-benzopyran-6-carbonitrile (2.17 g).

mp: 193° to 193.5° C. (dec.)

IR (Nujol): 3490, 3410, 3220, 2230, 2200, 1530 cm$^{-1}$ $[α]_D^{20}$: 206.10° (C=1, ethanol)

EXAMPLE 34

A mixture of (3R,4S)-4-(3-cyano-2-methyl-1-isothioureido)-3,4-dihydro-3-hydroxy-2,2-dimethyl-2H-1-benzopyran-6-carbonitrile (2.12 g) and 50% aqueous dimethylamine solution (10.6 ml) was stirred under reflux for 1.5 hours to form white precipitates. These precipitates were collected by filtration, washed with water, and recrystallized from ethanol to give (3R, 4S)-4 -(2-cyano-3,3-dimethylguanidino)-3,4-dihydro-3-hydroxy-2,2-dimethyl-2H-1-benzopyran-6-carbonitrile (1.03 g).

mp: 228° to 229° C.

IR (Nujol): 3360, 3250, 2220, 2180, 1580, 1520 cm$^{-1}$

NMR (DMSO-d$_6$, δ): 1.16 (3H, s), 1.41 (3H, s), 3.04 (6H, s), 3.64 (1H, dd, J=9 Hz, 6 Hz), 4.96 (1H, t, J=9 Hz), 5.76 (1H, d, J=6 Hz), 6.88 (1H, d, J=8 Hz), 7.15 (1H, d, J=9 Hz), 7.45-7.75 (1H, m)

$[α]_D^{23}$: +312.1° (C=1.0, methanol)

EXAMPLE 35

A mixture of (3S,4S)-3,4-epoxy-3,4-dihydro-2,2-dimethyl-2H-1-benzopyran-6-carbonitrile (0.603 g) and 2-cyanoiminothiazolidine (0.762 g) in triethylamine (4.2 ml) was heated under reflux for 9 hours. The resulting precipitates were collected by filtration, and washed with water, and recrystallized from ethanol to give (3S,4R)-4(2-cyanoiminothiazolidin-3-yl)-3,4-dihydro-3-hydroxy-2,2-dimethyl-2H-1-benzopyran-6-carbonitrile (0.56 g).

$[α]_D^{20}$: −78.3° (C=1, methanol)

EXAMPLE 36

A mixture of 3,4-epoxy-2,2-diethyl-3,4-dihydro-2H-1-benzopyran-6-carbonitrile (1.07 g) and 2-cyanoiminothiazolidine (0.89 g) in N,N-dimethylformamide-triethylamine (2:1, 7.5ml) was heated at 100° C. with stirring for 8 hours and 20 minutes. The reaction mixture was poured into water, extracted with ethyl acetate, washed with brine, and then dried over anhydrous magnesium sulfate. After the solution was evaporated in vacuo, the residue was purified with silica gel column chromatography using a mixture of ethyl acetate and n-hexane (1:1) as an eluent. The fractions containing the object compound were concentrated in vacuo and the residue was recrystallized from 50% aqueous acetonitrile to give trans-4-(2-cyanoiminothiazolidin-3-yl)-2,2-diethyl-3,4-dihydro-3-hydroxy-2H-1-benzopyran-6carbonitrile (0.48 g).

mp: 255° to 257° C. (dec.)

IR (Nujol): 3365, 2210, 2170, 1605, 1075 cm$^{-1}$

NMR (DMSO-d$_6$, δ): 0.85 (3H, t, J=7.3 Hz), 0.96 (3H, t, J=7.3 Hz), 1.35-2.00 (4H, m), 3.40-3.65 (2H, m), 3.75-3.° 95 (2H, m), 3.98 (1H, dd, J=6, 10 Hz), 5.37 (1H, d, J=10 Hz), 5.89 (1H, d, J=6 Hz), 7.01 (1H, d, J=8.5 Hz), 7.53 (1H, s), 7.66 (1H, d, J=8.5 Hz)

MASS: 338, 309

Anal. Calcd. for C$_{18}$H$_{20}$N$_4$O$_2$: C 60.65, H 5.66, N 15.72; Found: C 60.25, H 5.67, N 15.83

EXAMPLE 37

A mixture of trans-4-(2-cyanoiminothiazolidin-3-yl)-2,2-diethyl-3,4-dihydro-3-hydroxy-2H-1-benzopyran-6carbonitrile -(0.28 g) and acetic anhydride (0.15 ml) in pyridine (1.4 ml) was stirred overnight at ambient temperature. The reaction mixture was diluted with ethyl acetate, and then washed with 5% aqueous hydrochloric acid, saturated sodium bicarbonate solution and brine successively. The extract was dried over anhydrous magnesium sulfate and evaporated in vacuo to give a residue of trans-3-acetoxy-4-(2-cyanoiminothiazolidin-3-yl)-2,2-diethyl-3,4-dihydro-2H-1-benzopyran-6-carbonitrile, which was dissolved in toluene (12.5 ml) and thereto was added 1,8-diazabicyclo[5.4.0]undec-7-ene (0.35 ml). The reaction mixture was heated at 100° C. with stirring for an hour and 40 minutes. The solvent was evaporated in vacuo. The residue was triturated with ethyl acetate and recrystallized from 85% aqueous acetonitrile to give 4-(2-cyanoiminothiazolidin-3-yl)-2,2-diethyl-2H-1-benzopyran-6-carbonitrile (0.18 g).

mp: 251° to 252° C.

IR (Nujol) : 2225, 2180, 1662 cm$^{-1}$

NMR (Acetone-d$_6$, δ):0.96 (6H, t, J=8 Hz), 1.80 (4H, q, J=8 Hz), 3.79 (2H, t, J=7 Hz), 4.36 (2H, t, J=7 Hz), 6.02 (1H, s), 6.94 (1H, d, J=9 Hz), 7.49 (1H, s), 7.54 (1H, d, J=9 Hz)

MASS: 338, 309 Anal. Calcd. for C$_{18}$H$_{18}$N$_4$OS: C 63.88, H 5.36, N 16.56; Found: C 63.86, H 5.31, N 16.47

EXAMPLE 38

The following compounds were obtained according to a similar manner to that of Example 2.

(1) trans-3-Acetoxy-4-(2-cyano-3-methylguanidino)-3,4-dihydro-2,2-dimethyl-2H-1-benzopyran-6-carbonitrile mp: 223° to 227° C. (dec)

IR (Nujol): 3380, 3250, 2225, 2170, 1740, 1604, 1560 cm$^{-1}$

NMR (DMSO-d$_6$, δ): 1.24 (3H, s), 1.34 (3H, s), 2.07 (3H, s), 2.66 (3H, d, J=5 Hz), 4.99 (1H, d, J=9 Hz), 5.19 (1H, d, J=9 Hz), 6.96 (1H, d, J=8 Hz), 7.11-7.33 (2H, m), 7.56 (1H, br s), 7.61 (1H, dd, J=2, 8 Hz)

MASS: 281, 266

Anal. Calcd. for C$_{17}$H$_{19}$N$_5$O$_3$: C 59.81, H 5.61, N 20.52; Found; C 60.20, H 5.82, N 20.58

(2) trans-3-Acetoxy-4-2-cyanoimino-4,4-dimethylimidazolidin-1-yl)-3,4-dihydro-2,2-dimethyl-2H-1-benzopyran-6-carbonitrile mp: 228° to 231° C. (dec.)

IR (Nujol): 3210, 3160, 2225, 2175, 1750, 1610 cm$^{-1}$

NMR (DMSO-d$_6$, δ): 1.19 (3H, s), 1.27 (6H, s), 1.37 (3H, s), 2.10 (3H, s), 2.82 (1H, d, J=9 Hz), 3.22 [1H, d, J=9 Hz), 5.12 (2H, s), 7.01 (1H, d, J=9 Hz), 7.46 (1H, d, J=2 Hz), 7.66 (1H, dd, J=2, 9 Hz), 8.40 (1H, s)

MASS: 381, 380, 321, 306

EXAMPLE 39

The following compounds were obtained according to a similar manner to that of Example 3.

(1) 4-(2-Cyano-3-methylguanidino)-2,2-dimethyl-2H-1-benzopyran-6-carbonitrile mp: 240° to 243° C. (dec.)

IR (Nujol): 3300, 2225, 2190, 1680, 1600 cm$^{-1}$

NMR (DMSO-d$_6$, δ): 1.39 (6H, s), 2.91 (3H, s), 5.33 (1H, s), 6.99 (1H, d, J=8 Hz), 7.62 (1H, dd, J=2, 8 Hz), 7.80 (1H, d, J=2 Hz), 9.12 (1H, br s), 11.73 (1H, br s)

MASS: 281, 266

Anal. Calcd. for C$_{15}$H$_{15}$N$_5$O: C 64.04, H 5.37, N 24.89; Found: C 64.21, H 5.55, N 24.86

(2) 4-(2-Cyanoimino-4,4-dimethylimidazolidin-1-yl)-2-2-dimethyl-2H-1-benzopyran-6-carbonitrile.

mp: 250° to 252° C. (recrystallized from ethanol)

IR (Nujol): 3200, 3150, 2220, 2180, 1660, 1610 cm$^{-1}$

NMR (DMSO-d$_6$, δ): 1.38 (6H, s), 1.43 (6H, s), 3.58 (2H, s), 6.01 (1H, s), 6.93 (1H, d, J=9 Hz), 7.38 (1H, d, J=2 Hz), 7.59 (1H, dd, J=2, 9 Hz), 8.59 (1H, s)

MASS: 321, 306

Anal. Calcd. for C$_{18}$H$_{19}$N$_5$O: C 67.27, H 5.96, N 21.79; Found C 67.32, H 6.04, N 21.47

EXAMPLE 40

A mixture of trans-4-(2-cyano-3,3-dimethylguanidino)-3,4-dihydro-3-hydroxy-2,2-dimethyl-2H-1-benzopyran-6carbonitrile (0.76 g), methyl iodide (0.60 ml) and potassium carbonate (0.67 g) in N,N-dimethylformamide (4 ml) was heated at 80° C. for 5 hours. After cooling to the reaction mixture was added a mixture of ethyl acetate and water. The precipitate was cooled by filtration and recrystallized from ethanol to give trans-4-(2-cyano-1,3,3-trimethylguanidino)-3,4-dihydro-3-hydroxy-2,2- 0 dimethyl-2H-1-benzopyran-6-carbonitrile (0.11 g).

mp: 249° to 251° C. (dec.)

IR (Nujol): 3260, 2225, 2175, 1603, 1265, 1069 cm$^{-1}$

NMR (DMSO-d$_6$, δ): 1.16 (3H, s), 1.44 (3H, s), 2.58 (3H, s), 3.03 (6H, s), 3.70 (1H, dd, J=6, 10 Hz), 4.91 (1H, d, J=10 Hz), 5.86 (1H, d, J=6 Hz), 6.92 (1H, d, J=9 Hz), 7.49-7.72 (2H, m)

MASS: 327, 309, 294, 256

Anal. Calcd. for C$_{17}$H$_{21}$N$_5$O$_2$: C 62.37, H 6.47, N 21.39; Found: C 61.97, H 6.53, N 21.33

EXAMPLE 41

The following compounds were obtained according to a similar manner to that of Example 10.

(1) 4-(2-Cyano-1,3,3-trimethylguanidino)-2,2-dimethyl-2H-1-benzopyran-6-carbonitrile mp: 164° to 165° C.

IR (Nujol) 2230, 2175, 1640, 1605 (shoulder), 1280 cm$^{-1}$

NMR (DMSO-d$_6$, δ): 1.44 (6H, s), 2.86 (6H, s), 3.03 (3H, s), 5.72 (1H, s), 6.99 (1H, d, J=8 Hz), 7.47 (1H, d, J=2 Hz), 7.64 (1H, dd, J=2, 8 Hz)

MASS: 309, 294

Anal. Calcd. for C$_{17}$H$_{19}$N$_5$O: C 66.00, H 6.19, N 22.64; Found: C 66.22, H 6.18, N 22.86

(2) 4-(3-Benzyl-2-cyanoiminoimidazolidin-1-yl)-2,2-dimethyl-2H-1-benzopyran-6-carbonitrile mp: 177° to 179° C.

IR (Nujol): 2225, 2170, 1675, 1610, 1282 cm$^{-1}$

NMR (DMSO-d$_6$, δ): 1.50 (6H, s), 3.39-3.89 (4H, m), 4.51 (2H, s), 6.08 (1H, s), 6.91 (1H, d, J=8 Hz), 7.36 (5H, s), 7.60 (1H, dd, J=2, 8 Hz), 7.64 (1H, br s)

MASS: 383, 368, 292

Anal. Calcd. for C$_{23}$H$_{21}$N$_5$O: C 72.04, H 5.52, N 18.26; Found: C 71.99, H 5.68, N 18.37

EXAMPLE 42

The following compounds were obtained according to a similar manner to that of Example 1.

(1) trans-4-(2-Cyanoimino-4,4-dimethylimidazolidin-1-yl)-3,4-dihydro-3-hydroxy-2,2-dimethyl-2H-1-benzopyran-6-carbonitrile mp: 168° to 171° C.

IR (Nujol): 3560, 3230, 2225, 2175, 1610 cm$^{-1}$

NMR (DMSO-d$_6$, δ): 1.17 (3H, s), 1.30 (6H, s), 1.44 (3H, s), 2.89 (1H, d, J=9 Hz), 3.32 (1H, d, J=9 Hz), 3.78 (1H, dd, J=6, 10 Hz), 4.81 (1H, d, J=10 Hz), 5.79 (1H, d, J=6 Hz), 6.92 (1H, d, J=9 Hz), 7.33 (1H, d, J=2 Hz), 7.60 (1H, dd, J=2, 9 Hz), 8.27 (1H s)

MASS: 339, 321, 306

Anal. Calcd. for C$_{18}$H$_{21}$N$_5$O$_2$: C 63.70, H 6.24, N 20.63; Found: C 63.41, H 6.30, N 20.63

(2) trans-4-(3-Benzyl-2-cyanoiminoimidazolidin-1-yl)-3,4-dihydro-3-hydroxy-2,2-dimethyl-2H-1-benzopyran-6-carbonitrile mp: 250° to 253° C. (dec.)

IR (Nujol): 3305, 2225, 2175, 1610, 1079 cm$^{-1}$

NMR (DMSO-d$_6$, δ): 1.20 (3H, s), 1.46 (3H, s), 3.00-4.00 (5H, m), 4.60 (1H, d, J=16 Hz), 4.91 (1H, d, J=16 Hz), 5.35 (1H, br d, J=9 Hz), 5.89 (1H, d, J=6 Hz), 6.92 (1H, d, J=8 Hz), 7.36 (5H, br s), 7.49 (1H, d, J=2 Hz), 7.61 (1H, dd, J=2, 8 Hz)

MASS: 401, 383, 368, 330

Anal. Calcd. for C$_{23}$H$_{23}$N$_5$O$_2$: C 68.81, H 5.77, N 17.44; Found: C 68.18, H 5.85, N 17.08

(3) trans-4-(2-Cyanoiminooxazolidin-3-yl)-3,4-dihydro-3-hydroxy-2,2-dimethyl-2H-1-benzopyran-6-carbonitrile mp: 243° to 245° C. (dec.)

IR (Nujol): 3290, 2210, 2190, 1625, 1282 cm$^{-1}$

NMR (DMSO-d$_6$, δ): 1.19 (3H, s), 1.46 (3H, s), 3.25-3.50 (1H, m), 3.60-3.95 (2H, m), 4.60-4.75 (2H, m), 4.81 (1H, br d, J=10.3 Hz), 6.03 (1H, d, J=5.2 Hz0, 6.97 (1H, d, J=8.5 Hz), 7.65 (1H, dd, J=1.8, 8.5 Hz), 7.81 (1H, br s)

MASS: 313, 312, 294, 279

EXAMPLE 43

A mixture of 4-(2-cyanoiminoimidazolidin-1-yl)-2,2-dimethyl-2H-1-benzopyran-6-carbonitrile (0.59 g) and acetic anhydride (0.94 ml) in pyridine (5.9 ml) was stirred at 100° C. for 4 hours. The reaction mixture was cooled to room temperature and evaporated in vacuo.

The residue was dissolved in ethyl acetate, washed with 5% hydrochloric acid and brine, and dried over anhydrous magnesium sulfate. The solvent was evaporated in vacuo to give 4-(3-acetyl-2-cyanoiminoimidazolidin-1-yl)-2,2-dimethyl-2H-1-benzopyran-6-carbonitrile (0.41 g).

mp: 200° to 201° C.

IR (Nujol): 2220, 2170, 1690, 1655, 1620 cm$^{-1}$

NMR (DMSO-d$_6$, δ): 1.52 (6H, s), 2.45 (3H, s), 3.5–4.2 (4H, m), 6.26 (1H, s), 6.92 (1H, d, J=9 Hz), 7.63 (1H, dd, J=2, 9 Hz), 7.85 (1H, d, J=9 Hz)

MASS: 335, 320, 292, 278

Anal. Calcd. for $C_{18}H_{17}N_5O_2$: C 64.47, H 5.11, N 20.88; Found: C 64.18, H 5.13, N 20.81

What we claim is:

1. A compound of the formula:

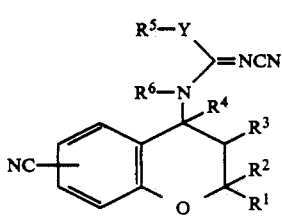

wherein
$R^1$ and $R^2$ are each lower alkyl,
$R^3$ is hydroxy or lower alkanoyloxy and $R^4$ is hydrogen, or
$R^3$ and $R^4$ are linked together to form a bond,
Y is —S—, —O— or a group of the formula

wherein $R^7$ is hydrogen, acyl, lower alkyl or mono or di or tri-phenyl(lower)alkyl, and
$R^5$ and $R^6$ are each hydrogen or lower alkyl, or
$R^5$ and $R^6$ are linked together to form lower alkylene, or pharmaceutically acceptable salt thereof.

2. A compound of claim 1, in which
$R^3$ is hydroxy or lower alkanoyloxy and $R^4$ is hydrogen, or
$R^3$ and $R^4$ are linked together to form a bond, and Y is —S—, —O— or a group of the formula:

wherein $R^7$ is hydrogen, lower alkanoyl, lower alkyl or phenyl.

3. A compound of claim 2, in which
Y is —S—, —O— or a group of the formula:

wherein
$R^7$ is hydrogen, lower alkanoyl, lower alkyl or phenyl(lower)alkyl, and
$R^5$ and $R^6$ are each hydrogen or lower alkyl.

4. A compound of claim 3, in which
$R^3$ is hydroxy, $R^4$ is hydrogen, and
Y is —S—, —O— or a group of the formula:

wherein $R^7$ is hydrogen or lower alkyl.

5. A compound of claim 4, which is selected from the group consisting of:
trans-4-(2-cyano-3-methylguanidino)-3,4-dihydro-3-hydroxy-2,2-dimethyl-2H-1-benzopyran-6-carbonitrile, and
trans-4-(2-cyano-3,3-dimethylguanidino)-3,4-dihydro-3-hydroxy-2,2-dimethyl-2H-1-benzopyran-6-carbonitrile.

6. A compound of claim 3, in which
$R^3$ and $R^4$ are linked together to form a bond, and
Y is —S—, —O— or a group of the formula:

wherein $R^7$ is hydrogen or lower alkyl.

7. A compound of claim 6, which is selected from the group consisting of
4-(2-cyano-3-methylguanidino)-2,2-dimethyl-2H-1-benzopyran-6-carbonitrile, and
4-(2-cyano-3,3-dimethylguanidino)-2,2-dimethyl-2H1-benzopyran-6-carbonitrile.

8. A compound of claim 2, in which
Y is —S—, —O— or a group of the formula:

wherein
$R^7$ is hydrogen, lower alkanoyl, lower alkyl or phenyl(lower)alkyl, and
$R^5$ and R are linked together to form lower alkylene.

9. A compound of claim 8, in which
$R^3$ is hydroxy and $R^4$ is hydrogen, and
Y is —S—, —O— or a group of the formula:

wherein $R^7$ is hydrogen or lower alkyl.

10. A compound of claim 9, which is selected from the group consisting of
trans-4-(2-cyanoiminoimidazolidin-1-yl)-3,4-dihydro-3-hydroxy-2,2-dimethyl-2H-1-benzopyran-6-carbonitrile, and
trans-4-(2-cyanoiminothiazolidin-3-yl)-3,4-dihydro-3-hydroxy-2,2-dimethyl-2H-1-benzopyran-6-carbonitrile.

11. A compound of claim 10, which is (3S,4R)-4-(2-cyanoiminothiazolidin-3-yl)-3,4-dihydro-3-hydroxy-2,2-dimethyl-2H-1-benzopyran-6-carbonitrile.

12. A compound of claim 8, in which
$R^3$ and $R^4$ are linked together to form a bond, and
Y is —S—, —O— or a group of the formula:

wherein R⁷ is hydrogen or lower alkyl.

13. A compound of claim 12, which is selected from the group consisting of:

4-(2-cyanoiminoimidazolidin-1-yl)-2,2-dimethyl-2H-1-benzopyran-6-carbonitrile, and 4-(2-cyanoiminothiazolidin-3-yl}-2,2-dimethyl-2H1-benzopyran-6-carbonitrile.

14. An antihypertensive pharmacuetical composition which comprises, as an active ingredient, an effective amount of a compound of claim 1 or a pharmaceutically acceptable salt thereof in admixture with a pharmaceutically acceptable carrier.

15. A method for the treatment of hypertension which comprises administering an effective amount of a compound of claim 1 or a pharmaceutically acceptable salt thereof to a human or animal.

* * * * *